(12) United States Patent
Djupesland

(10) Patent No.: US 9,272,104 B2
(45) Date of Patent: Mar. 1, 2016

(54) NASAL DELIVERY

(75) Inventor: Per Gisle Djupesland, Oslo (NO)

(73) Assignee: OptiNose AS, Oslo (NO)

( * ) Notice: Subject to any disclaimer, the term of this patent is extended or adjusted under 35 U.S.C. 154(b) by 1155 days.

(21) Appl. No.: 12/293,972

(22) PCT Filed: Mar. 23, 2007

(86) PCT No.: PCT/IB2007/001998
§ 371 (c)(1),
(2), (4) Date: Aug. 27, 2009

(87) PCT Pub. No.: WO2007/107887
PCT Pub. Date: Sep. 27, 2007

(65) Prior Publication Data
US 2009/0320832 A1    Dec. 31, 2009

(30) Foreign Application Priority Data

Mar. 23, 2006    (GB) .................................. 0605799.6

(51) Int. Cl.
*A61M 11/00*    (2006.01)
*A61M 15/08*    (2006.01)
*A61M 15/00*    (2006.01)

(52) U.S. Cl.
CPC ........... *A61M 15/08* (2013.01); *A61M 15/0003* (2014.02); *A61M 15/0098* (2014.02); *A61M 11/00* (2013.01); *A61M 15/009* (2013.01); *A61M 15/0065* (2013.01); *A61M 2202/064* (2013.01); *A61M 2205/075* (2013.01); *A61M 2210/0618* (2013.01); *A61M 2210/0625* (2013.01)

(58) Field of Classification Search
CPC .......................... A61M 15/08; A61M 15/0098
USPC ............. 128/200.23, 200.14, 200.18, 200.22; 604/93.01, 94.01
See application file for complete search history.

(56) References Cited

U.S. PATENT DOCUMENTS

| 5,437,267 A * | 8/1995 | Weinstein et al. ....... 128/200.23 |
| 5,797,390 A | 8/1998 | McSoley |
| 5,901,703 A * | 5/1999 | Ohki et al. ............... 128/203.12 |
| 6,491,940 B1 | 12/2002 | Levin |
| 6,715,485 B1 | 4/2004 | Djupesland |

(Continued)

FOREIGN PATENT DOCUMENTS

| EP | 1 410 820 A | 4/2004 | |
| EP | 1410820 A2 * | 4/2004 | ............ A61M 15/08 |

(Continued)

OTHER PUBLICATIONS

U.S. Appl. No. 11/567,286, filed Dec. 6, 2006, Djupesland.

(Continued)

*Primary Examiner* — Kristen Matter
(74) *Attorney, Agent, or Firm* — Finnegan, Henderson, Farabow, Garrett and Dunner, LLP

(57) ABSTRACT

A delivery device for and method of delivering a dose of substance for systemic uptake to a nasal cavity of a subject, the delivery device comprising: a nosepiece unit for insertion into a nasal cavity of a subject and comprising an outlet unit which includes at least one nozzle for delivering substance for systemic uptake substantially only to surfaces in one or both of the anterior region and an anterior section of the posterior region of the nasal cavity of the subject; and a substance supply unit which is operable to deliver a dose of substance to the at least one nozzle.

18 Claims, 21 Drawing Sheets

(56) References Cited

U.S. PATENT DOCUMENTS

| | | |
|---|---|---|
| 7,347,201 B2 | 3/2008 | Djupesland |
| 7,377,901 B2 | 5/2008 | Djupesland et al. |
| 7,469,700 B2 * | 12/2008 | Baran .................... 128/207.14 |
| 7,481,218 B2 | 1/2009 | Djupesland |
| 7,543,581 B2 | 6/2009 | Djupesland |
| 2004/0112378 A1 | 6/2004 | Djupesland |
| 2004/0112379 A1 | 6/2004 | Djupesland |
| 2004/0182388 A1 | 9/2004 | Djupesland |
| 2005/0028812 A1 | 2/2005 | Djupesland |
| 2005/0072430 A1 | 4/2005 | Djupesland |
| 2005/0235992 A1 | 10/2005 | Djupesland |
| 2005/0281751 A1 | 12/2005 | Levin |
| 2006/0096589 A1 | 5/2006 | Djupesland |
| 2006/0169278 A1 | 8/2006 | Djupesland |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2007/0039614 A1 | 2/2007 | Djupesland |
| 2007/0125371 A1 | 6/2007 | Djupesland |
| 2007/0186927 A1 | 8/2007 | Djupesland et al. |
| 2008/0161771 A1 | 7/2008 | Djupesland |
| 2008/0163874 A1 | 7/2008 | Djupesland |
| 2008/0221471 A1 | 9/2008 | Djupesland |
| 2008/0223363 A1 | 9/2008 | Djupesland |
| 2008/0289629 A1 | 11/2008 | Djupesland |
| 2009/0101146 A1 | 4/2009 | Djupesland |

FOREIGN PATENT DOCUMENTS

| | | |
|---|---|---|
| GB | 2378393 | 2/2003 |
| WO | 00/51672 | 9/2000 |
| WO | 03/020350 | 3/2003 |
| WO | 03/090812 | 11/2003 |
| WO | 2004/004814 | 10/2004 |
| WO | 2007/099361 | 9/2007 |

OTHER PUBLICATIONS

U.S. Appl. No. 11/816,984, filed Aug. 23, 2007, Djupesland.
U.S. Appl. No. 12/161,466, filed Jul. 18, 2008, Djupesland.
U.S. Appl. No. 12/279,285, filed Aug. 13, 2008, Djupesland.
U.S. Appl. No. 12/279,291, filed Aug. 13, 2008, Djupesland.
U.S. Appl. No. 12/281,547, filed Sep. 3, 2008, Djupesland.
U.S. Appl. No. 12/281,894, filed Sep. 5, 2008, Djupesland.
U.S. Appl. No. 12/298,292, filed Oct. 23, 2008, Djupesland.
U.S. Appl. No. 12/303,667, filed Dec. 5, 2008, Djupesland.
U.S. Appl. No. 12/375,115, filed Jan. 26, 2009, Djupesland.
U.S. Appl. No. 12/516,399, filed May 27, 2009, Djupesland.
U.S. Appl. No. 12/516,401, filed May 27, 2009, Djupesland.
U.S. Appl. No. 12/516,404, filed May 27, 2009, Djupesland.
International Search Report for International App. No. PCT/IB2007/001998, Mailed Nov. 7, 2007 (4 pages).
International Preliminary Report on Patentability for International App. No. PCT/IB2007/001998 (8 pages).

* cited by examiner

NASAL DELIVERY

The present invention relates to a nasal delivery device for and a method of intranasally delivering substances for systemic uptake, as liquids, such as suspensions or solutions, and powders, where containing medicaments, typically pharmaceuticals, or vaccines.

Figure 1A:
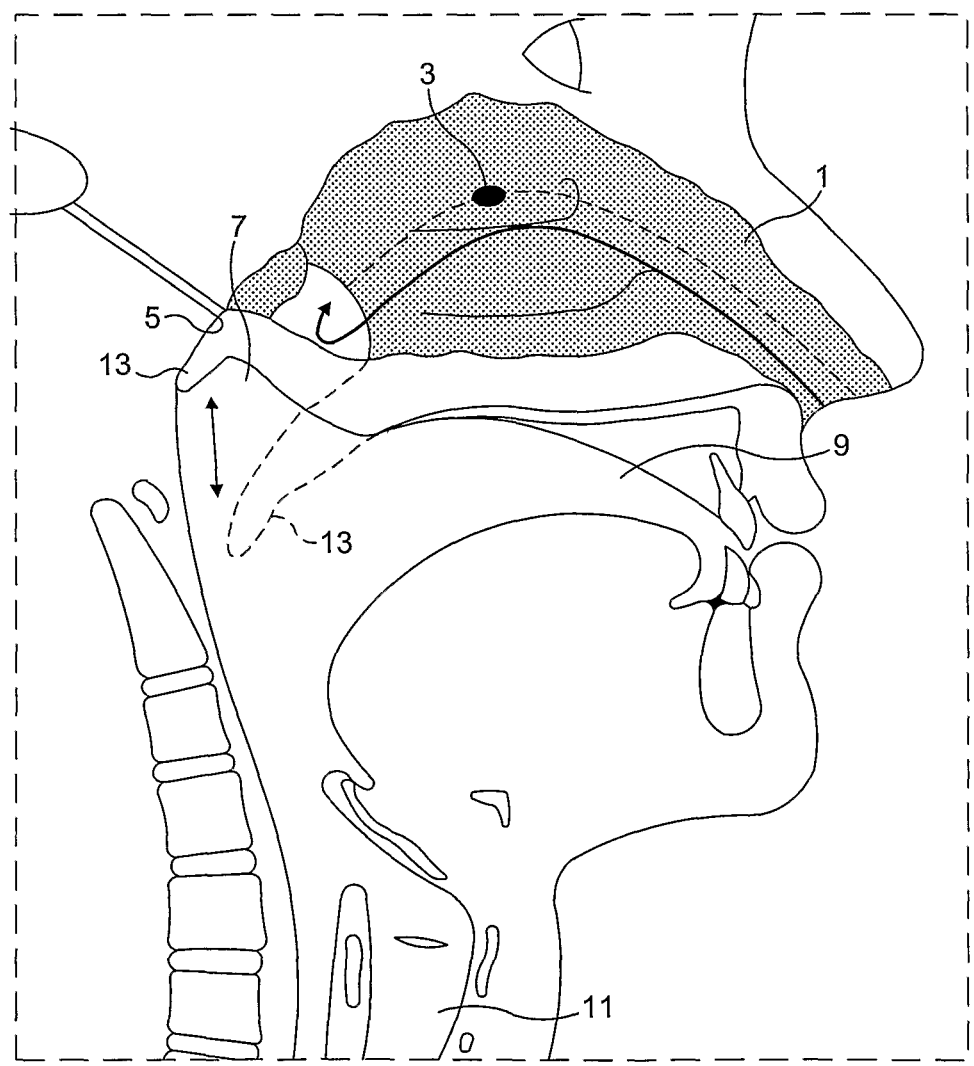

Referring to FIG. 1(a), the nasal airway 1 comprises the two nasal cavities separated by the nasal septum, which airway 1 includes numerous ostia, such as the paranasal sinus ostia 3 and the tubal ostia 5, and olfactory cells, and is lined by nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

Figure 1B:
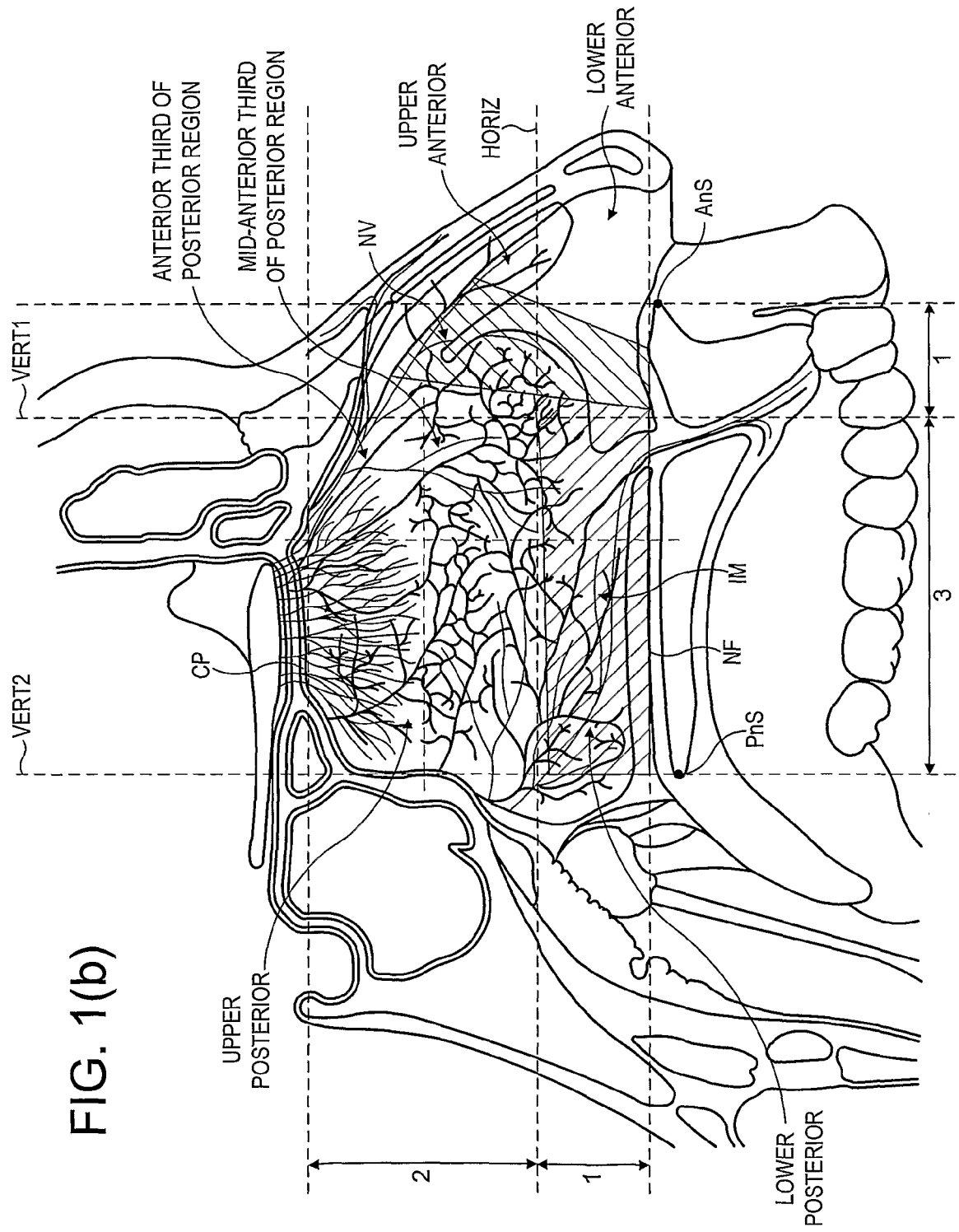

The nasal cavities each comprise a posterior region which is that region which is posterior of the nasal valve NV and an anterior region which is that region which is anterior of the nasal valve NV, as illustrated in FIG. 1(b).

The nasal valve NV comprises the anterior bony cavum which contains inferior turbinate erectile tissue and septal erectile tissue, which are supported respectively by compliant ala tissue and the rigid cartilaginous septum [Cole]. These elements combine to form a dynamic valve, which extends over several millimeters, that adjusts nasal airflow, and is stabilized by cartilage and bone, modulated by voluntary muscle and regulated by erectile tissue. The lumen of the nasal valve NV is the section of narrowest cross-sectional area between the posterior and anterior regions of the nasal airway, and is much longer and narrower dorsally than ventrally, and this lumen defines a triangular entrance which extends to the piriform region of the bony cavum. The nasal valve NV is lined in its anterior part with transitional epithelium, with a gradual transition posterior to respiratory epithelium. The nasal valve NV and anterior vestibule define roughly the anterior one-third of the nose.

The posterior region of the nasal airway is that region which is lined with respiratory epithelium, which is ciliated, and olfactory epithelium, which comprises nerves which extend downwards through the cribiform plate CP from the olfactory bulb, whereas the anterior region of the nasal airway is that region which is lined with squamous epithelium, which is not ciliated, and transitional epithelium, and extends to the skin-lined section at the nares of the nostril. The olfactory epithelium extends on both the lateral and medial sides of the nasal airway, and typically extends downwards about 1.5 to 2.5 cm.

As illustrated in FIG. 1(b), the posterior region of the nasal airway is the nasal region posterior of an imaginary vertical plane VERT1 which is located at a position corresponding to one-quarter of the distance between the anterior nasal spine AnS, which is a pointed projection at the anterior extremity of the intermaxillary suture, and the posterior nasal spine PnS, which is the sharp posterior extremity of the nasal crest of the hard palate and represents the transition between the nose and the nasopharynx, which corresponds to a distance posterior of the anterior nasal spine AnS of between about 13 mm and about 14 mm [Rosenberger defines the distance between the anterior nasal spine AnS and the posterior nasal spine PnS as being 56 mm in eighteen year old boys and 53.3 mm in eighteen year old girls]. As again illustrated in FIG. 1(b), the posterior nasal region is bounded posteriorly by an imaginary vertical plane VERT2 which extends through the posterior nasal spine PnS.

The upper posterior region is the region above the inferior meatus IM, as illustrated in FIG. 1(b), and encompasses the middle turbinate, the sinus ostia in infundibulum (ostia to maxillary, frontal and ethmoidal sinuses), the olfactory region, and the upper branches of the trigeminal nerve, and is that region which includes veins which drain to the venous sinuses that surround the brain.

As further illustrated in FIG. 1(b), the upper region of the nasal airway is an upper segment of the nasal airway which is bounded by the cribiform plate CP and a horizontal plane HORIZ which is located at a position corresponding to one-third of the distance between the nasal floor NF of the nasal airway and the cribiform plate CP, which corresponds to a height of typically between about 13 and about 19 mm above the nasal floor NF [Zacharek et al define the distance from the nasal floor NF to the cribiform plate CP as 46 +/−4 mm].

The upper posterior region is thus that upper posterior region which is bounded by the above-defined vertical and horizontal planes VERT1, HORIZ.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion.

Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal tissues advantageously provides for rapid systemic uptake.

In relation to systemic delivery, studies [Daley-Yates et al and Harris et al] have shown that significantly increased systemic bio-availability is achieved by delivery as a nasal spray as compared to drops.

Daley-Yates et al investigated the systemic bio-availability of fluticasone propionate where delivered both as an aqueous spray and as nasal drops, and the bio-availability of the nasal spray formulation was about eight times higher than that of the nasal drop formulation. The authors of the this study have attributed this increased bio-availability of the nasal spray formulation to the by-passing of the nose and an increased absorption from the gastro-intestinal (GI) tract, where the nose is by-passed by one or both of mucociliary clearance of the substance or sniffing the substance along the floor of the nose and subsequent swallowing.

Harris et al investigated the intranasal administration of desmopressin as a nasal spray and as nasal drops, and the bio-availability of the nasal spray formulation was two to three times higher than that of the nasal drop formulation.

In line with these studies, the current understanding in the art is that to achieve maximal absorption of substance to the systemic circulation, the substance should be delivered to as large a surface of the nasal cavity as possible.

The present inventors have now contrarily and surprisingly recognized that the delivery of substance to the anterior region of the nasal cavity and an anterior section of the posterior region of the nasal cavity, in particular the anterior third, and more particularly the mid-anterior third of the posterior region, predominantly influences the systemic bio-availability of the substance, and, by controlling the delivery of the substance to the anterior region of the nasal cavity and the anterior section of the posterior region of the nasal cavity, a more uniform and increased bio-availability can be achieved for a given dose of the substance. A particular problem of existing delivery regimes is the significant variability in the systemic bio-availability, which the present inventors attribute to the significant variation in the distribution of substance as delivered in subject to subject. The present inventors have recognized that delivering the dose of substance in particular to the anterior region of the nasal cavity can provide a desired uniformity to the systemic bio-availability.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. As discussed hereinabove, a particular advantage of the present invention is the reliability in the dosing. This is particularly the case even in the event of a congested nose, such as with a cold or an allergy, as delivery is to the anterior region, which is not congested, though there may be some secretion.

WO-A-00/51672 discloses a delivery device for delivering substance, in particular a medicament, in a bidirectional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

It is an aim of the present invention to provide improved nasal delivery devices and nasal delivery methods, which in particular provide for one or both of increased systemic bio-availability of the delivered substance and improved dose-to-dose uniformity in the systemic bio-availability.

In one aspect the present invention provides a delivery device for delivering a dose of substance for systemic uptake to a nasal cavity of a subject, the delivery device comprising: a nosepiece unit for insertion into a nasal cavity of a subject and comprising an outlet unit which includes at least one nozzle for delivering substance for systemic uptake substantially only to surfaces in one or both of the anterior region and an anterior section of the posterior region of the nasal cavity of the subject; and a substance supply unit which is operable to deliver a dose of substance to the at least one nozzle.

In another aspect the present invention provides a method of delivering a dose of substance for systemic uptake to a nasal cavity of a subject, the method comprising the steps of: disposing a nosepiece unit in the nasal cavity of the subject, the nosepiece unit comprising at least one nozzle for delivering substance for systemic uptake to surfaces substantially only in one or both of the anterior region and an anterior section of the posterior region of the nasal cavity of the subject; and delivering a dose of substance from a substance supply unit to the at least one nozzle, such that the substance is delivered to surfaces substantially only in one or both of the anterior region and an anterior section of the posterior region.

Figure 2:
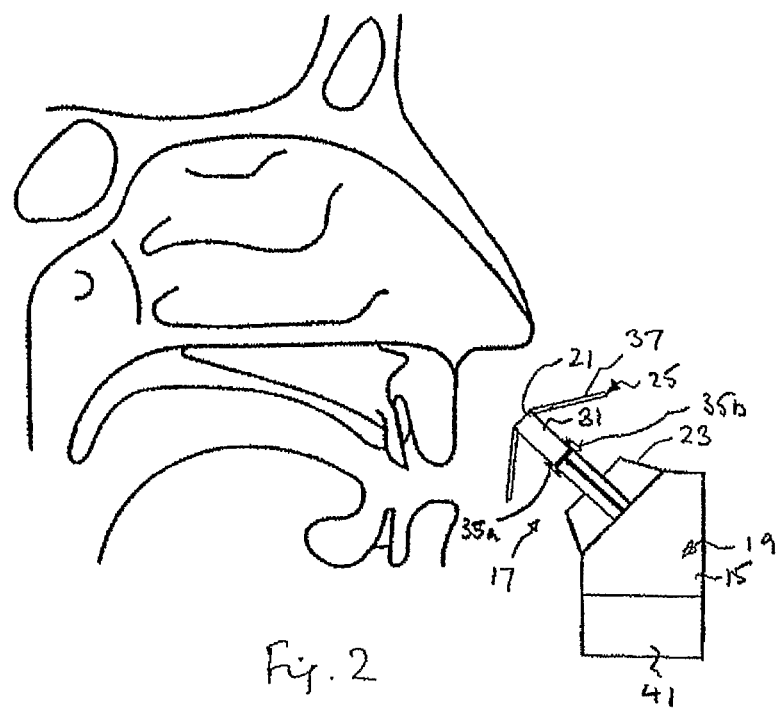
Figure 3:
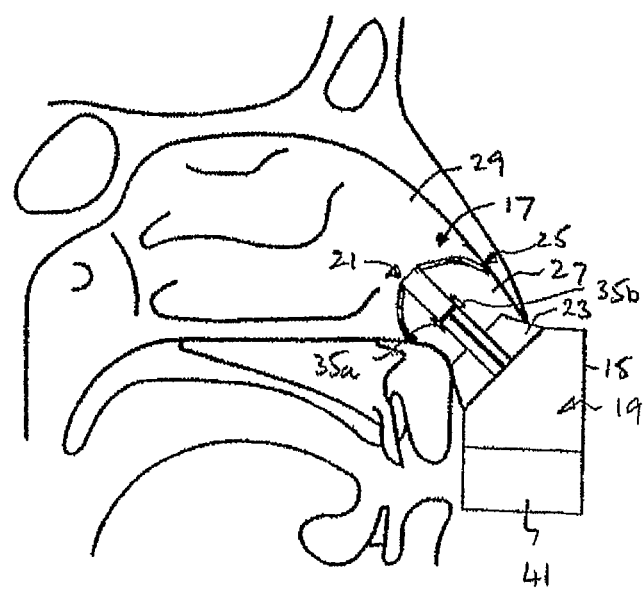
Figure 4:
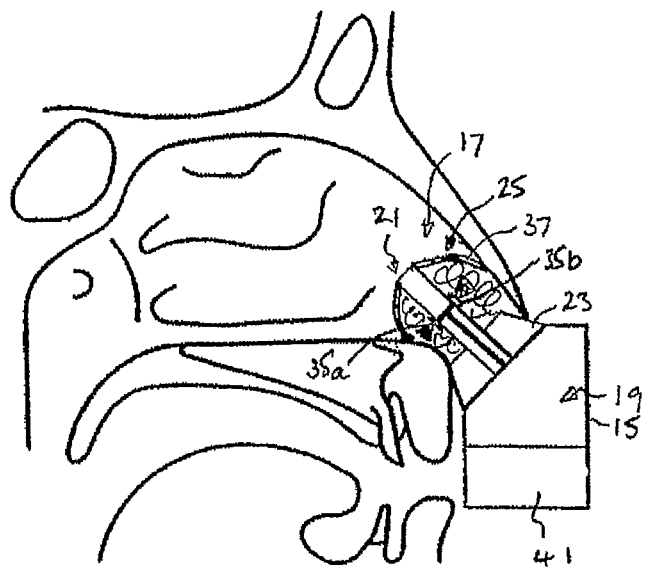
Figure 5:
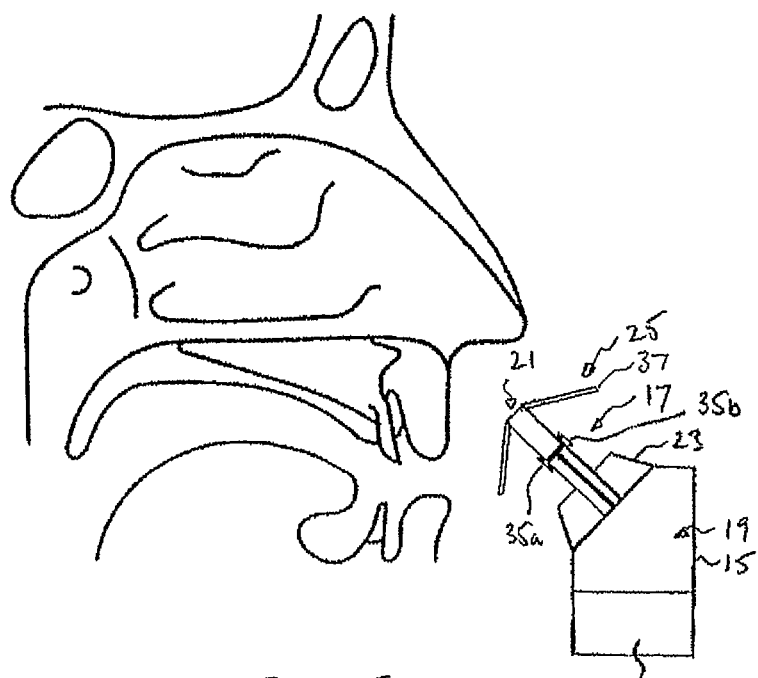
Figure 6:
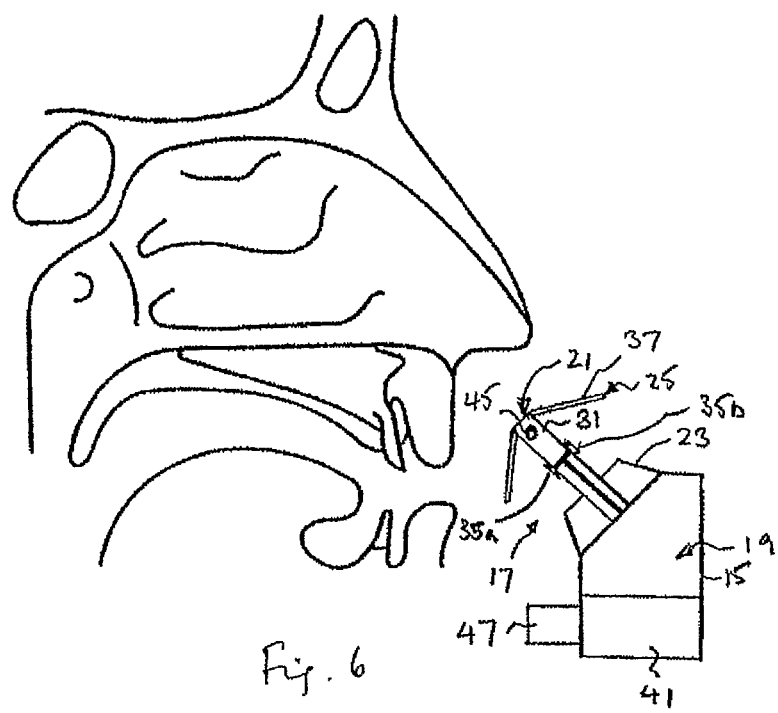
Figure 7:
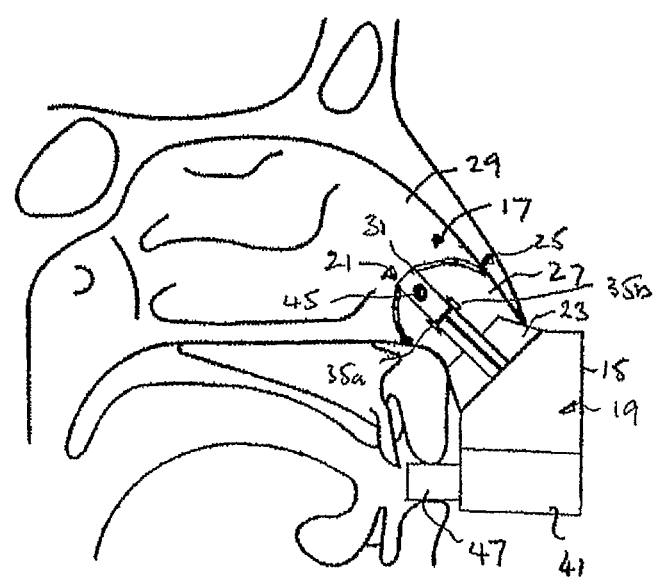
Figure 8:
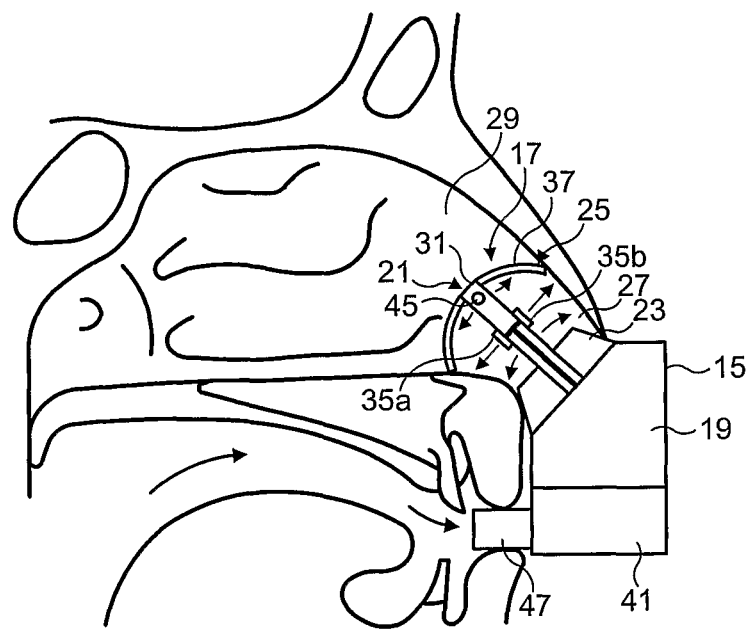
Figure 9:
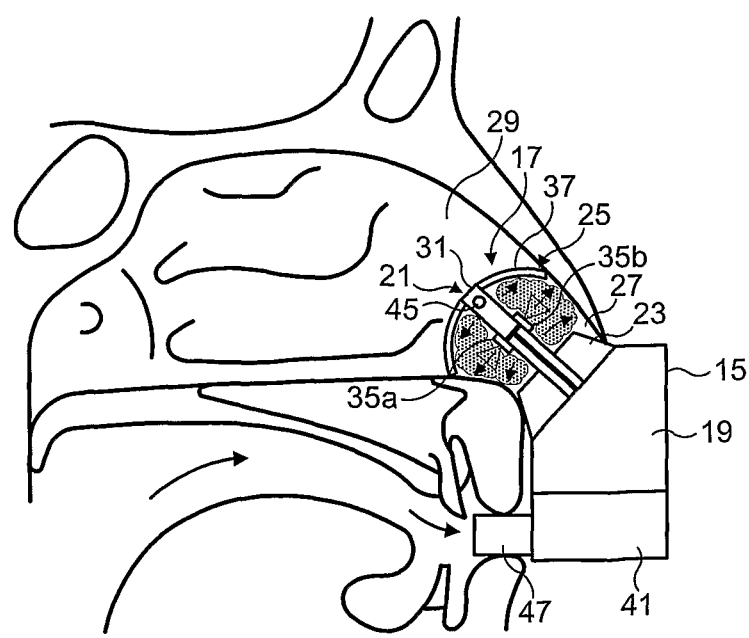
Figure 10:
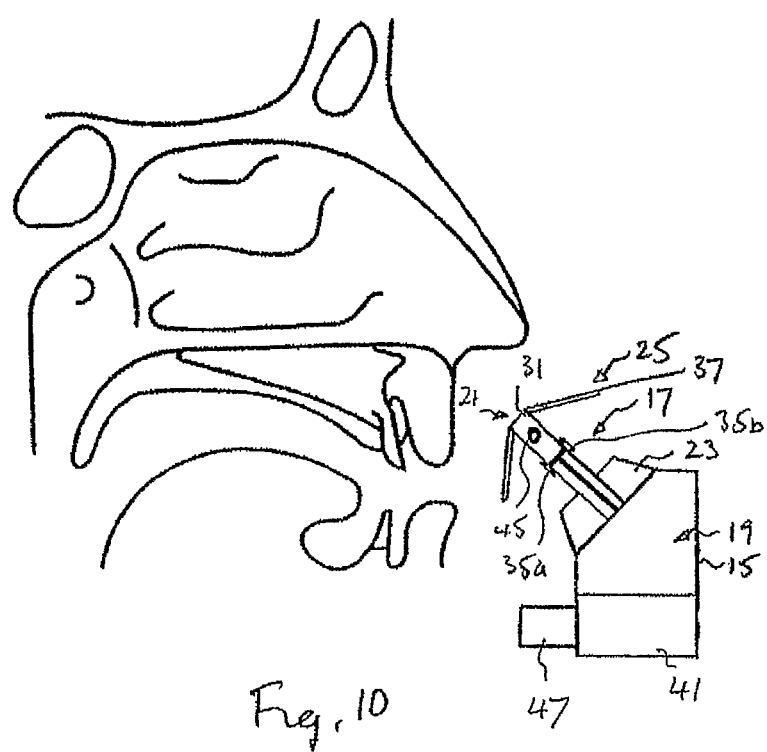
Figure 11:
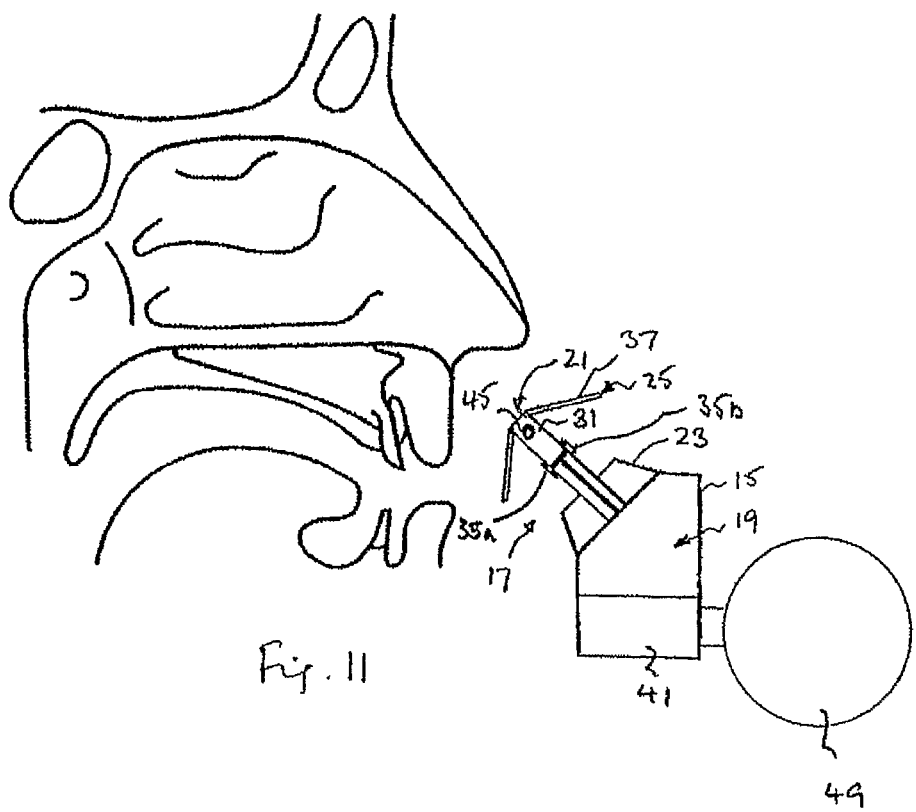
Figure 12:
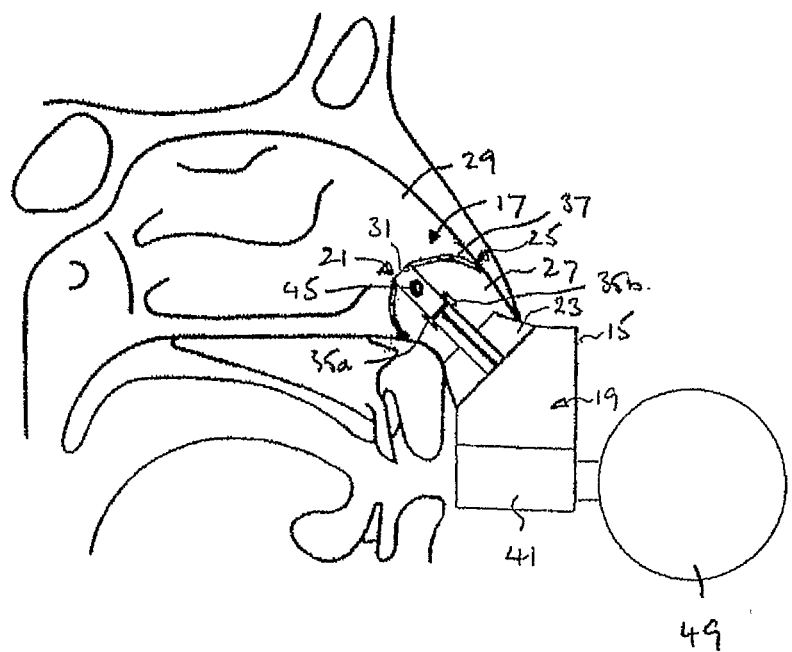
Figure 13:
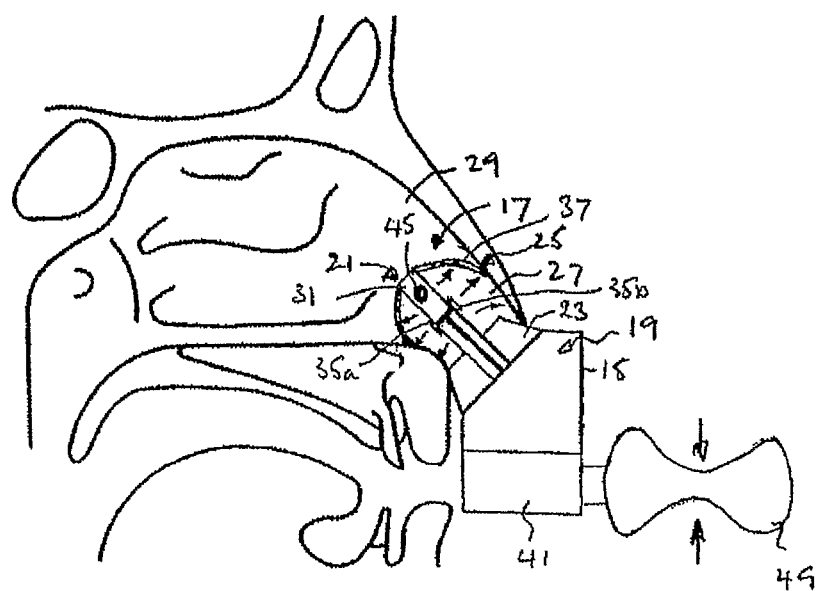
Figure 14:
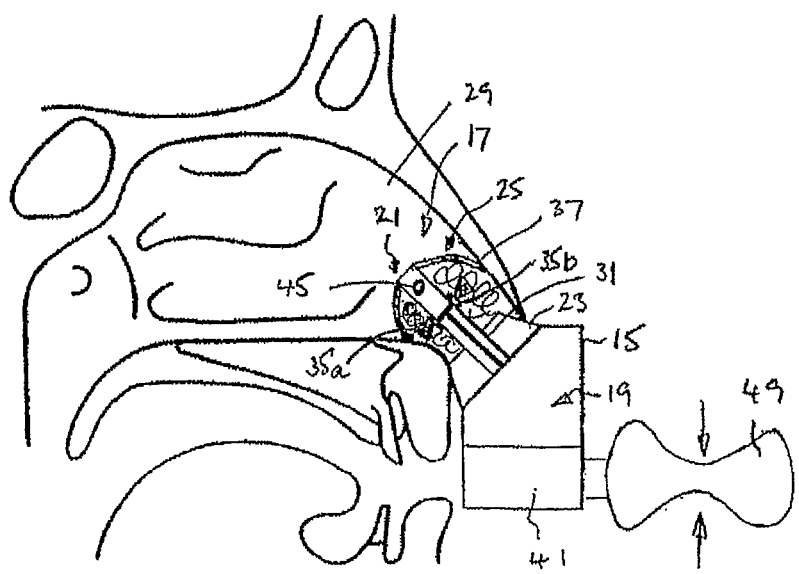
Figure 15:
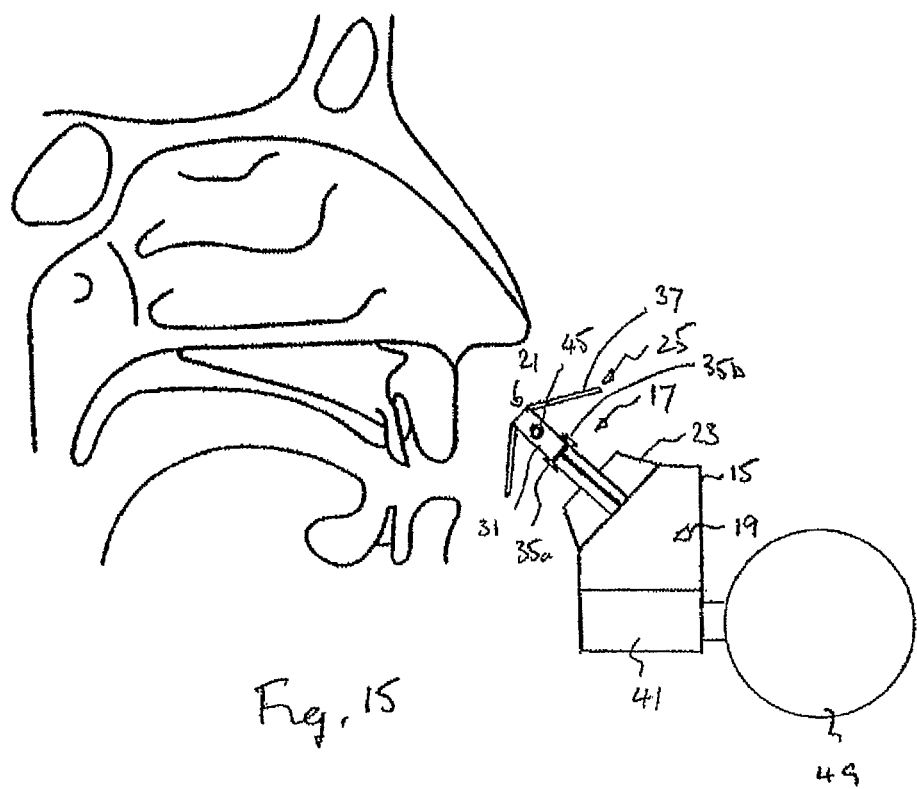
Figure 16:
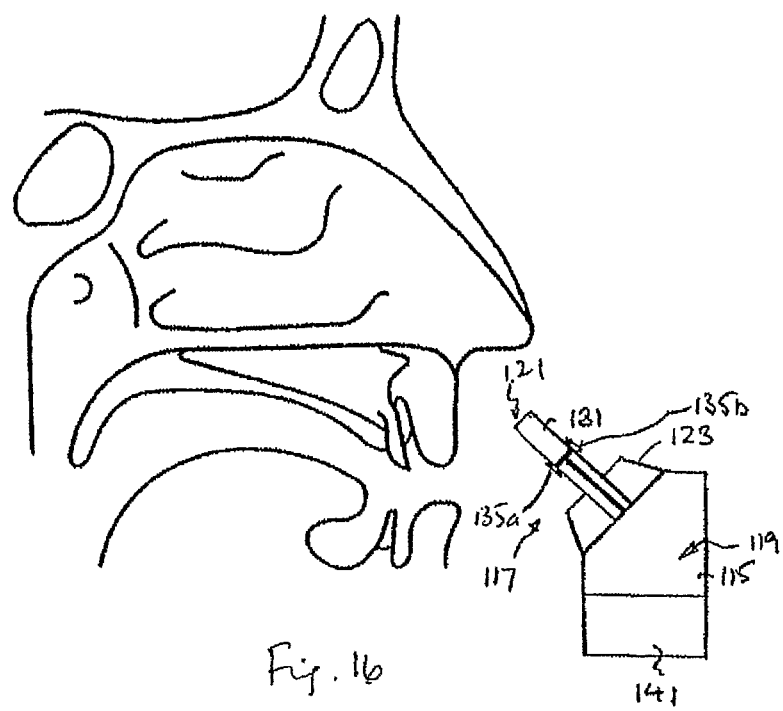
Figure 17:
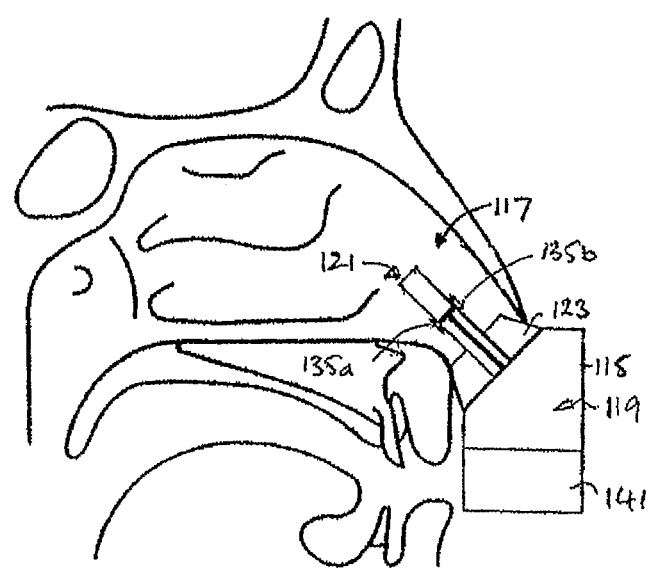
Figure 18:
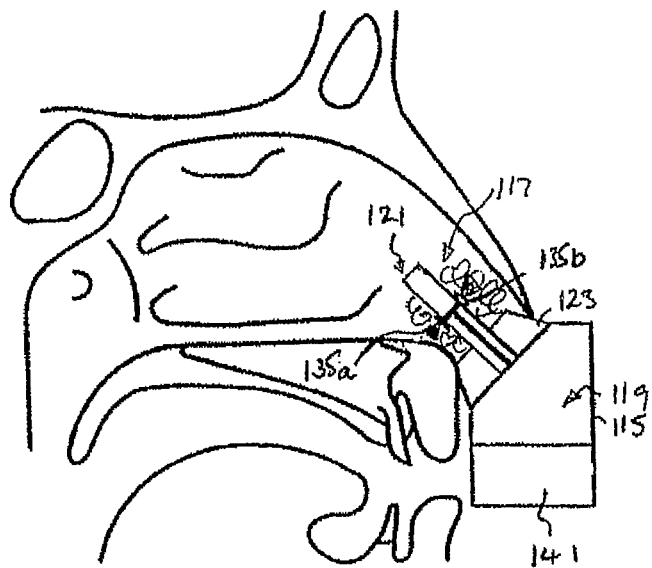
Figure 19:
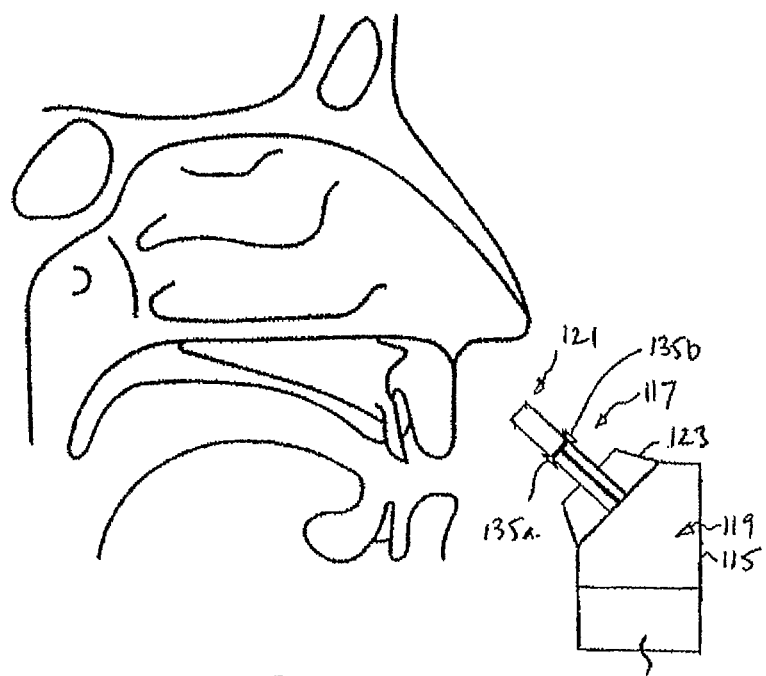
Figure 20:
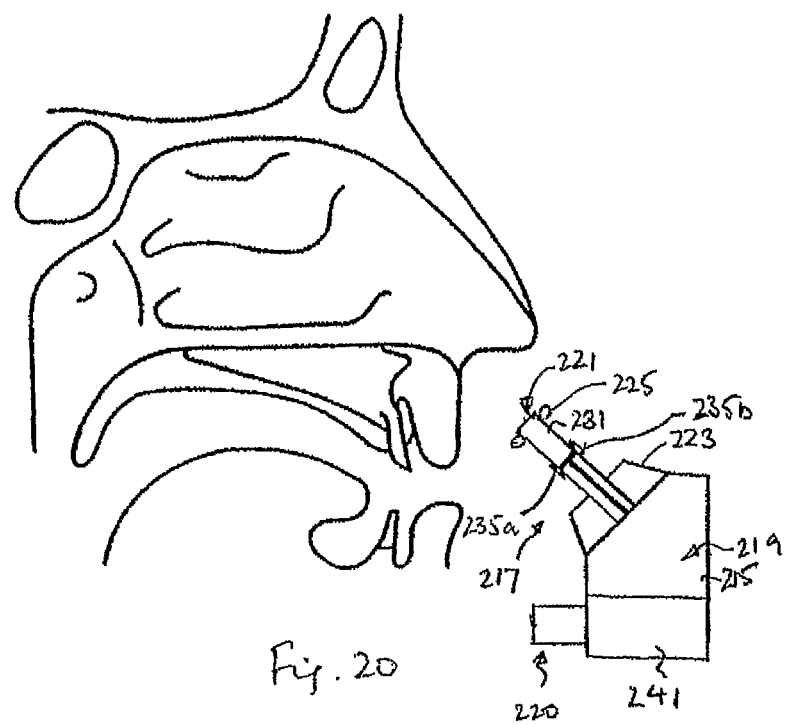
Figure 21:
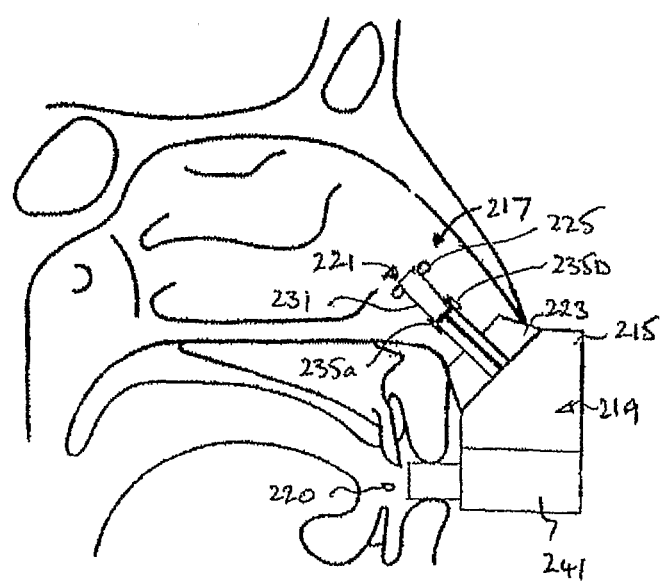
Figure 22:
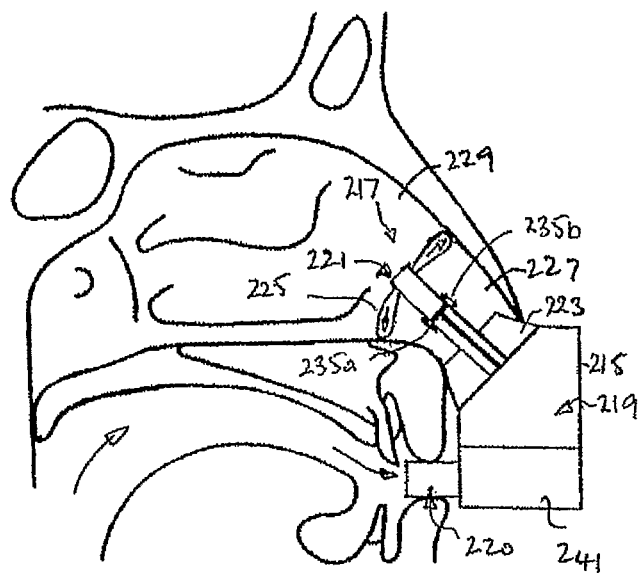
Figure 23:
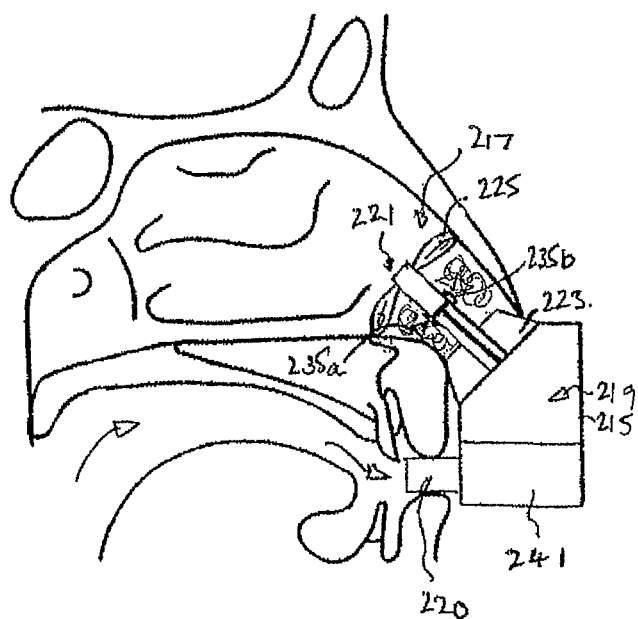
Figure 24:
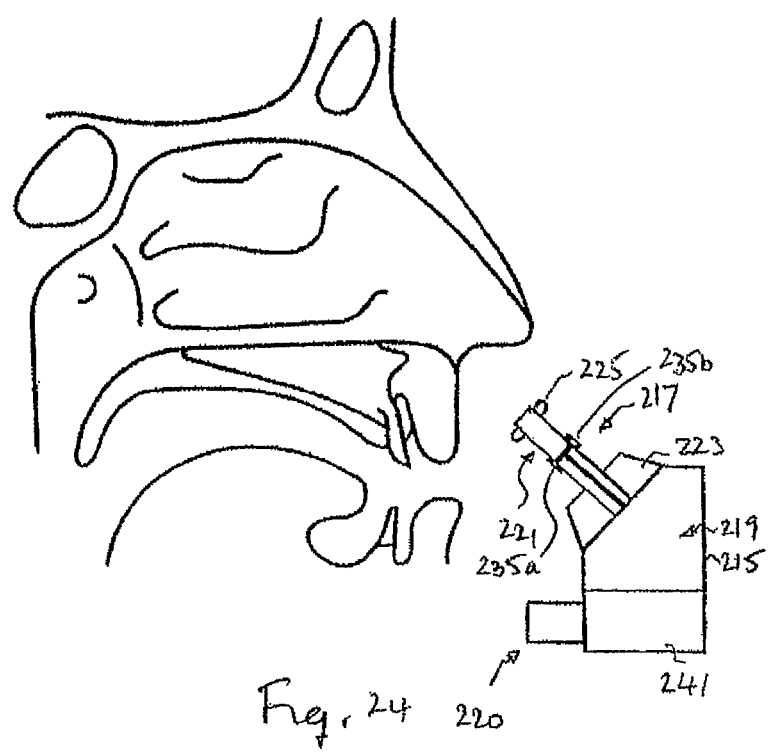
Figure 25:
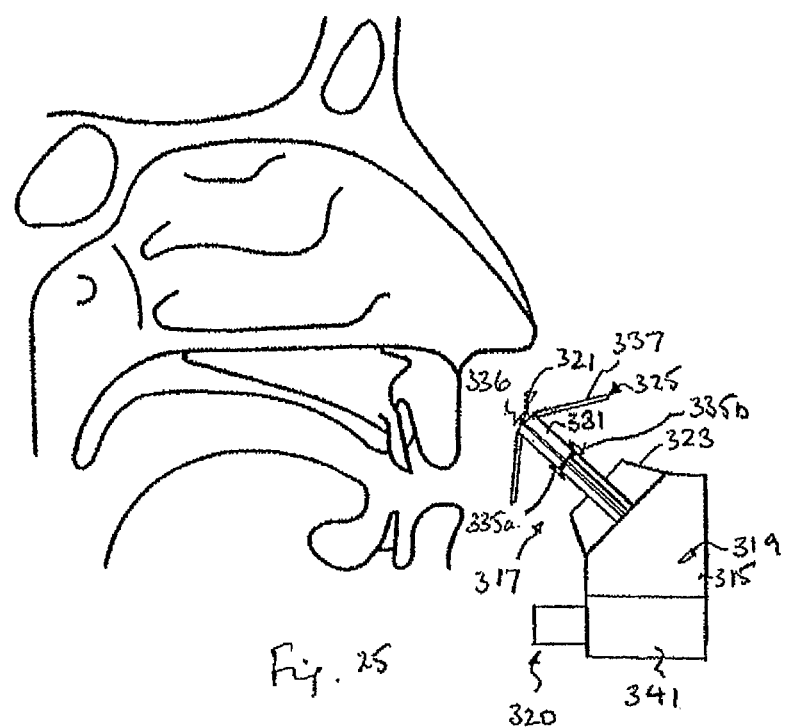
Figure 26:
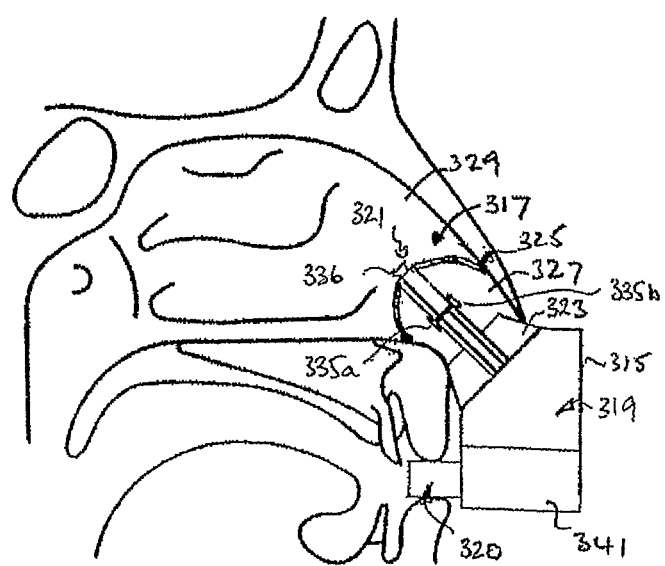
Figure 27:
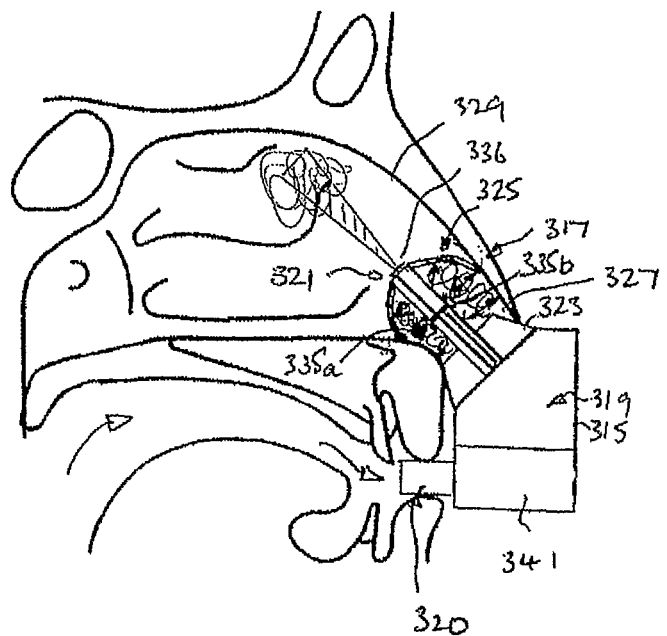
Figure 28:
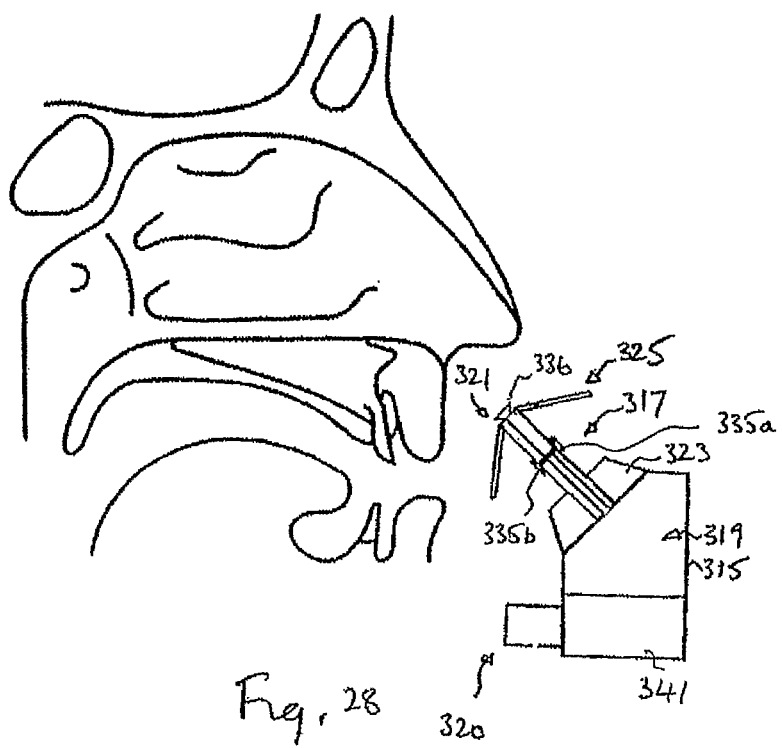
Figure 29:
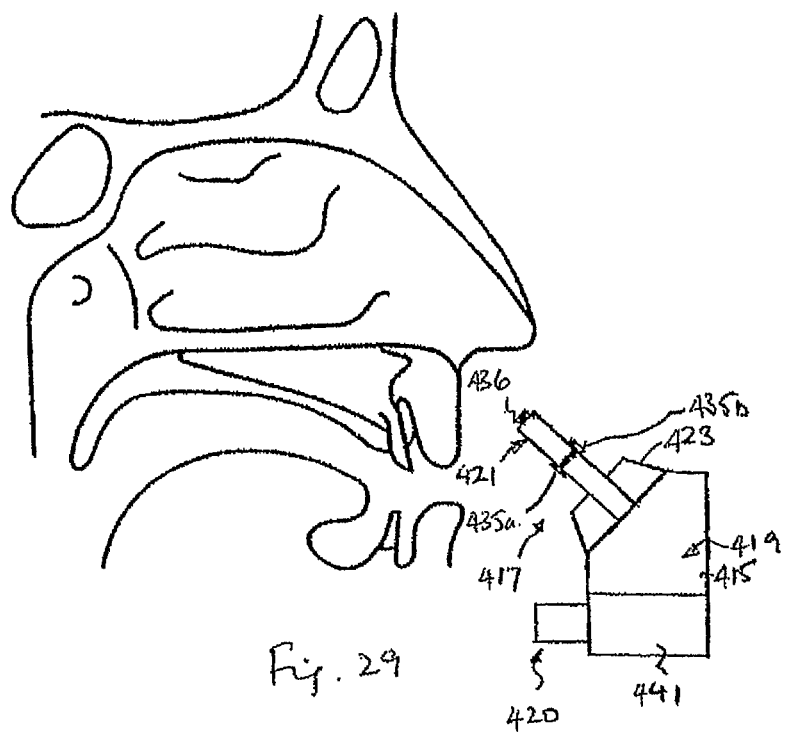
Figure 30:
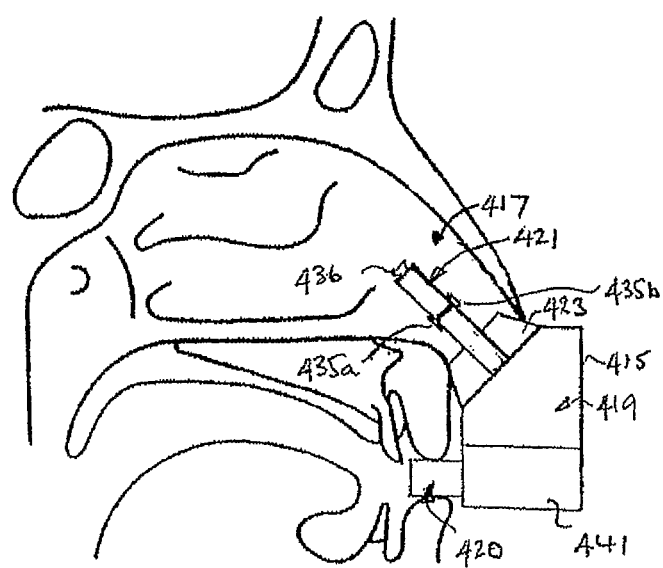
Figure 31:
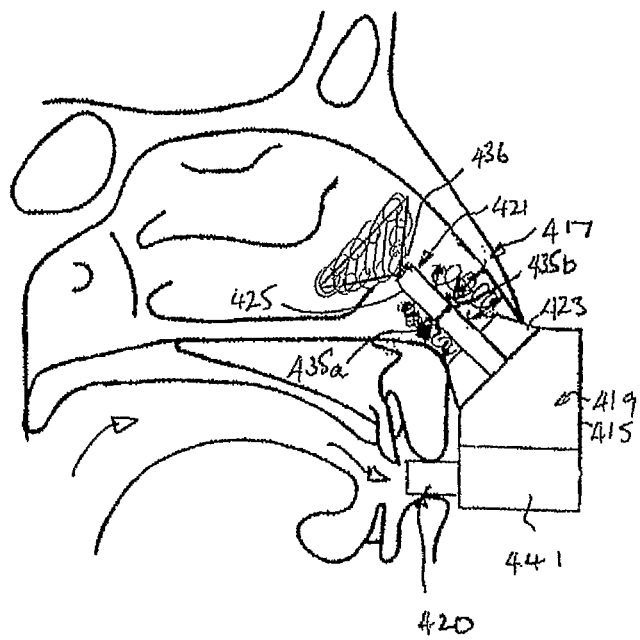
Figure 32:
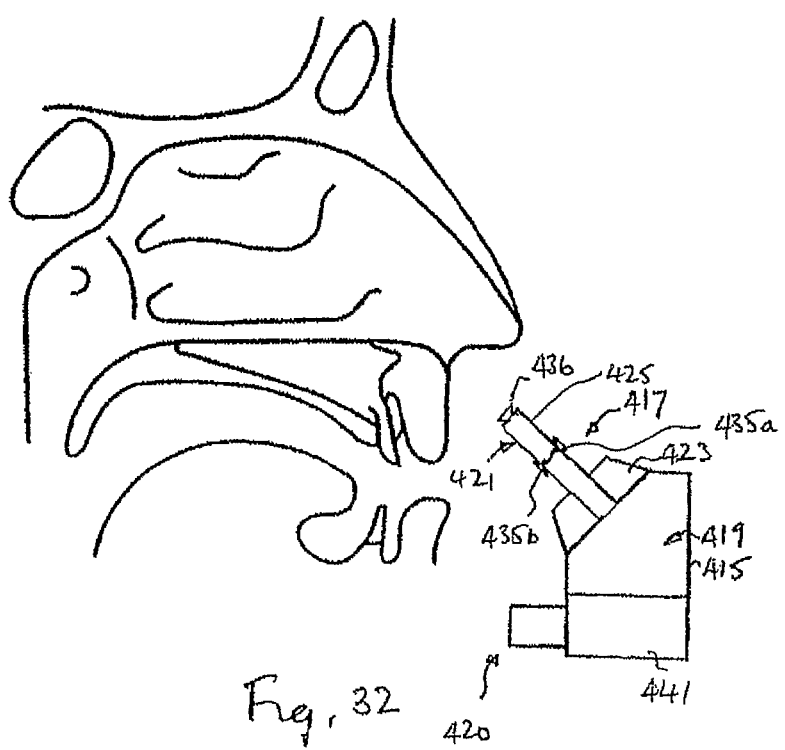
Figure 33:
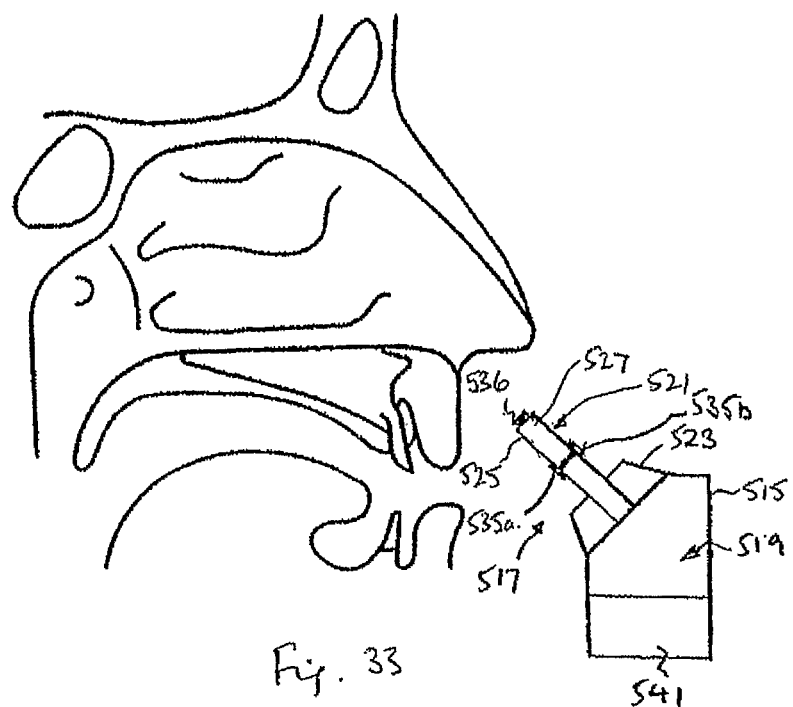
Figure 34:
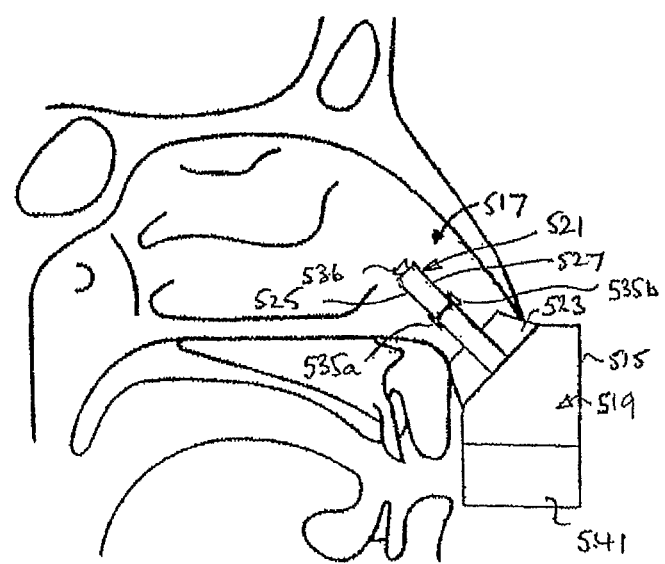
Figure 35:
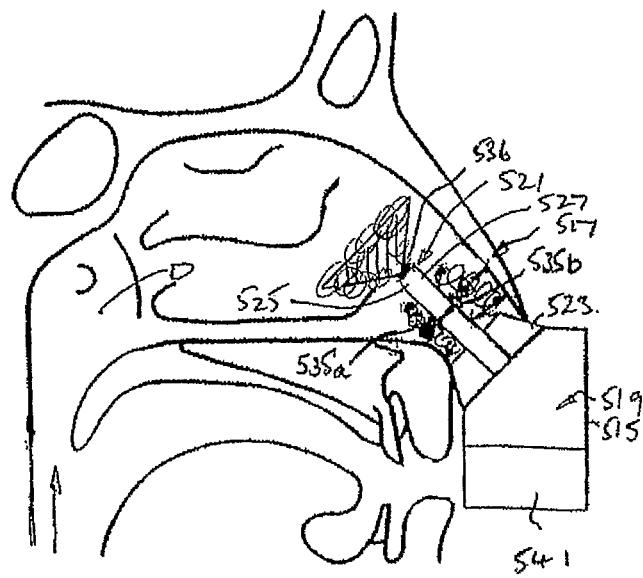
Figure 36:
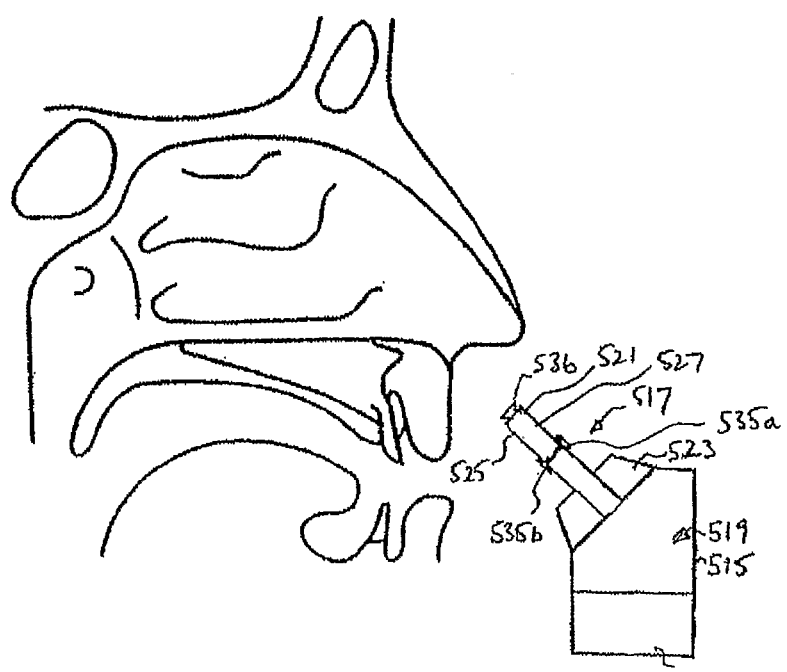

Preferred embodiments of the present invention will now be described hereinbelow by way of example only with reference to the accompanying drawings, in which:

FIG. 1(a) schematically illustrates the anatomy of the upper respiratory tract of a human subject;

FIG. 1(b) illustrates the segmentation of a nasal cavity in accordance with a preferred embodiment of the present invention;

FIG. 2 schematically illustrates a nasal delivery device in accordance with a first embodiment of the present invention;

FIG. 3 schematically illustrates the delivery device of FIG. 2 inserted in a nasal cavity of a subject for operation;

FIG. 4 schematically illustrates the delivery device of FIG. 2 during actuation;

FIG. 5 schematically illustrates the delivery device of FIG. 2 following actuation;

FIG. 6 schematically illustrates a nasal delivery device in accordance with a second embodiment of the present invention;

FIG. 7 schematically illustrates the delivery device of FIG. 6 inserted in a nasal cavity of a subject for operation;

FIG. 8 schematically illustrates the delivery device of FIG. 6 during a first actuation phase in which a positive pressure is created in the anterior region by the exhalation breath;

FIG. 9 schematically illustrates the delivery device of FIG. 6 during a second actuation phase in which the substance supply unit is actuated to deliver substance into the anterior region;

FIG. 10 schematically illustrates the delivery device of FIG. 6 following actuation;

FIG. 11 schematically illustrates a nasal delivery device in accordance with a third embodiment of the present invention;

FIG. 12 schematically illustrates the delivery device of FIG. 11 inserted in a nasal cavity of a subject for operation;

FIG. 13 schematically illustrates the delivery device of FIG. 11 during a first actuation phase in which a positive pressure is created in the anterior region by the exhalation breath;

FIG. 14 schematically illustrates the delivery device of FIG. 11 during a second actuation phase in which the substance supply unit is actuated to deliver substance into the anterior region;

FIG. 15 schematically illustrates the delivery device of FIG. 11 following actuation;

FIG. 16 schematically illustrates a nasal delivery device in accordance with a fourth embodiment of the present Invention;

FIG. 17 schematically illustrates the delivery device of FIG. 16 inserted in a nasal cavity of a subject for operation;

FIG. 18 schematically illustrates the delivery device of FIG. 16 during actuation;

FIG. 19 schematically illustrates the delivery device of FIG. 16 following actuation;

FIG. 20 schematically illustrates a nasal delivery device in accordance with a fifth embodiment of the present invention;

FIG. 21 schematically illustrates the delivery device of FIG. 20 inserted in a nasal cavity of a subject for operation;

FIG. 22 schematically illustrates the delivery device of FIG. 20 during a first actuation phase in which the second nosepiece member of the nosepiece unit is inflated by the exhalation breath of the subject such as to partition the nasal cavity;

FIG. 23 schematically illustrates the delivery device of FIG. 20 during a second actuation phase in which the substance supply unit is actuated to deliver substance into the anterior region;

FIG. 24 schematically illustrates the delivery device of FIG. 20 following actuation;

FIG. 25 schematically illustrates a nasal delivery device in accordance with a sixth embodiment of the present invention;

FIG. 26 schematically illustrates the delivery device of FIG. 25 inserted in a nasal cavity of a subject for operation;

FIG. 27 schematically illustrates the delivery device of FIG. 25 during actuation;

FIG. 28 schematically illustrates the delivery device of FIG. 25 following actuation;

FIG. 29 schematically illustrates a nasal delivery device in accordance with a seventh embodiment of the present invention;

FIG. 30 schematically illustrates the delivery device of FIG. 29 inserted in a nasal cavity of a subject for operation;

FIG. 31 schematically illustrates the delivery device of FIG. 29 during actuation;

FIG. 32 schematically illustrates the delivery device of FIG. 29 following actuation;

FIG. 33 schematically illustrates a nasal delivery device in accordance with an eighth embodiment of the present invention;

FIG. 34 schematically illustrates the delivery device of FIG. 33 inserted in a nasal cavity of a subject for operation;

FIG. 35 schematically illustrates the delivery device of FIG. 33 during actuation; and FIG. 36 schematically illustrates the delivery device of FIG. 33 following actuation.

FIGS. 2 to 5 illustrate a nasal delivery device in accordance with a first embodiment of the present invention.

The delivery device comprises a housing 15, a nosepiece unit 17 for fitting in a nasal cavity of a subject through which substance is delivered to the nasal cavity, and a substance supply unit 19 which is actuatable to deliver a metered dose of substance to the nosepiece unit 17.

The nosepiece unit 17 comprises an outlet unit 21 which extends into the nasal cavity into which the nosepiece unit 17 is inserted, a first nosepiece member 23, in this embodiment a frusto-conical element, which is disposed to one, proximal end of the outlet unit 21 and is configured to obstruct, in this embodiment close, the nostril into which the nosepiece unit 17 is inserted, a second nosepiece member 25 which is disposed to the other, distal end of the outlet unit 21 and is configured to obstruct, in this embodiment close, the nasal cavity at a position therealong, in this embodiment at a position corresponding substantially to the nasal valve, such as to partition the nasal cavity into a first, anterior region 27 between the first and second nosepiece members 23, 25, which corresponds in volume to about one-third of the nasal cavity, and a second, posterior region 29, which corresponds in volume to about the remaining two-thirds of the nasal cavity, as illustrated In FIG. 3.

The outlet unit 21 comprises a support member 31, in this embodiment a narrow, elongate element, to which the first and second nosepiece members 23, 25 are supported, and at least one nozzle 35, in this embodiment a plurality of laterally-directed nozzles 35a, b, disposed between the first and second nosepiece members 23, 25 for delivering substance to the anterior region 27 of the nasal cavity.

In this embodiment the nozzles 35a, b are configured to provide an aerosol spray. In an alternative embodiment the nozzles 35a, b could be configured to deliver jets as columns of substance.

In this embodiment the second nosepiece member 25 comprises a resilient element 37, here in the form of an annular skirt, which through its resilience acts to expand to obstruct the nasal cavity in partitioning the same. In an alternative embodiment the resilient element 37 could take the form of laterally-directed wings, which together act to obstruct the nasal cavity in partitioning the same.

In this embodiment the substance supply unit 19 comprises a mechanical delivery pump, in particular a liquid delivery pump or a powder delivery pump, which delivers metered doses of substance on actuation thereof.

In another alternative embodiment the substance supply unit 19 could comprise a dry powder delivery unit which delivers metered doses of substance, as a dry powder, on actuation thereof.

In yet another alternative embodiment the substance supply unit 19 could comprise an aerosol canister which delivers metered volumes of a propellant, preferably a hydrofluoroalkane (HFA) propellant or the like, containing substance, either as a suspension or solution.

In yet another alternative embodiment the substance supply unit 19 could comprise a nebulizer which delivers metered doses of substance, as an aerosol spray, on actuation thereof.

In this embodiment the substance supply unit 19 is a multi-dose unit for delivering a plurality of metered doses of substance. In another embodiment the substance supply unit 19 could be a single-dose unit for delivering a single metered dose of substance, In this embodiment the substance supply unit 19 is pre-primeable, here by loading a resilient element, and includes an actuation mechanism 41 which, when triggered, releases the resilient element and actuates the substance supply unit 19 to deliver a metered dose of substance through the nozzles 35*a, b* of the outlet unit 21.

Operation of the delivery device will now be described hereinbelow with reference to FIGS. 3 to 5 of the accompanying drawings.

Referring to FIG. 3, the nosepiece unit 17 is first inserted into one of the nasal cavities of a subject until the first nosepiece member 23 abuts the nares of the nostril, such as sealingly to engage the skin-lined anterior section of the anterior region of the nasal cavity. When inserted, the distal end of the outlet unit 21 extends about 2 cm into the nasal cavity of the subject, which corresponds in position to that of the nasal valve, and the second nosepiece member 25 acts to obstruct the nasal cavity at that point such as to partition the nasal cavity.

Referring to FIG. 4, the subject then actuates the actuation mechanism 41, in this embodiment manually, which acts to actuate the substance supply unit 19 to deliver a metered dose of substance from the nozzles 35*a,* 35*b* of the outlet unit 21.

The metered dose of substance, in this embodiment in the form of an aerosol spray, is confined to the anterior region 27 of the nasal cavity as defined between the first and second nosepiece members 23, 25. As described hereinabove, the present inventors have recognized that the systemic uptake of substance as delivered via the nasal cavity is, contrary to current thinking, enhanced where delivered through the anterior region of the nasal cavity, and thus, by confining the delivered dose of substance to the anterior region, an enhanced systemic effect is obtained per unit dose of substance as compared to the conventional delivery of substances into the nasal cavity, such as generally by a nasal spray or nasal drops.

Following actuation, as illustrated in FIG. 5, the nosepiece unit 17 is withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 19. In a preferred embodiment, where the nosepiece unit 17 is replaceable, the nosepiece unit 17 can be replaced with a new nosepiece unit 17.

FIGS. 6 to 10 illustrate a nasal delivery device in accordance with a second embodiment of the present invention.

The delivery device of this embodiment is very similar to the delivery device of the above-described embodiment, and thus, in order to avoid unnecessary duplication of description, only the differences will be described in detail.

The delivery device of this embodiment differs from that of the above-described embodiment in that the support member 31 of the outlet unit 21 includes a gas delivery port 45 which is disposed at a position between the first and second nosepiece members 23, 25, and in further comprising a mouthpiece 47 which is fluidly connected to the gas delivery port 45, such that, on exhalation into the mouthpiece 47, an air flow is delivered to the gas delivery port 45 which acts to develop a pressure in the partitioned anterior region 27 as defined between the first and second nosepiece members 23, 25, which acts to expand the anterior region 27 and thereby promote the delivery of substance thereto.

Operation of the delivery device is illustrated in FIGS. 7 to 10 of the accompanying drawings. The operation of the delivery device of this embodiment is the same as that of the above-described embodiment, except in that the subject exhales through the mouthpiece 47 during actuation of the delivery device, in order to cause expansion of the partitioned anterior section.

In one alternative-embodiment the actuation mechanism 41 could be a breath-actuated mechanism, such that the actuation mechanism 41 acts to actuate the substance supply unit 19 on the generation of a predetermined pressure at the mouthpiece 47.

FIGS. 11 to 15 illustrate a nasal delivery device in accordance with a third embodiment of the present invention.

The delivery device of this embodiment is very similar to the delivery device of the above-described embodiment, and thus, in order to avoid unnecessary duplication of description, only the differences will be described in detail.

The delivery device of this embodiment differs from that of the above-described embodiment in that the support member 31 of the outlet unit 21 includes a gas delivery port 45 which is disposed at a position between the first and second nosepiece members 23, 25, and in further comprising a gas supply unit 49, in this embodiment a compressible bulb, which is fluidly connected to the gas delivery port 45 and actuatable to deliver an air flow to the gas delivery port 45 which acts to develop a pressure in the partitioned anterior region 27 as defined between the first and second nosepiece members 23, 25, which acts to expand the anterior region 27 and thereby promote the delivery of substance thereto.

Operation of the delivery device is illustrated in FIGS. 12 to 15 of the accompanying drawings. The operation of the delivery device of this embodiment is the same as that of the above-described embodiment, except in that the subject actuates the gas supply unit 49, in this embodiment by compressing the bulb, during actuation of the delivery device, in order to cause expansion of the partitioned anterior region 27.

FIGS. 16 to 19 illustrate a nasal delivery device in accordance with a fourth embodiment of the present invention.

The delivery device comprises a housing 115, a nosepiece unit 117 for fitting in a nasal cavity of a subject through which substance is delivered to the nasal cavity, and a substance supply unit 119 which is actuatable to deliver a metered dose of substance to the nosepiece unit 117.

The nosepiece unit 117 comprises an outlet unit 121 which extends into the nasal cavity into which the nosepiece unit 117 is inserted, and a nosepiece member 123, in this embodiment a frusto-conical element, which is disposed to one, proximal end of the outlet unit 121 and is configured to obstruct, in this embodiment close, the nostril into which the nosepiece unit 117 is inserted.

The outlet unit 121 comprises a support member 131, in this embodiment a narrow, elongate element, to which the nosepiece member 123 is supported, and at least one nozzle 135, in this embodiment a plurality of laterally-directed nozzles 135*a, b*, which is disposed such as to deliver substance substantially entirely to the anterior region 137 of the nasal cavity relative to the posterior region of the nasal cavity 139. By configuring the at least one nozzle 135 such as to direct the substance laterally to the surfaces of the anterior region 137 of the nasal cavity, the substance is substantially entirely delivered to the anterior region 137 of the nasal cavity relative to the posterior region 139 of the nasal cavity.

In this embodiment the nozzles 135*a, b* are configured to provide an aerosol spray. In an alternative embodiment the nozzles 135*a, b* could be configured to deliver jets as columns of substance.

In this embodiment the substance supply unit 119 comprises a mechanical delivery pump, in particular a liquid delivery pump or a powder delivery pump, which delivers metered doses of substance on actuation thereof.

In another alternative embodiment the substance supply unit 119 could comprise a dry powder delivery unit which delivers metered doses of substance, as a dry powder, on actuation thereof.

In yet another alternative embodiment the substance supply unit 119 could comprise an aerosol canister which delivers metered volumes of a propellant, preferably a hydrofluoroalkane (HFA) propellant or the like, containing substance, either as a suspension or solution.

In yet another alternative embodiment the substance supply unit 119 could comprise a nebulizer which delivers metered doses of substance, as an aerosol spray, on actuation thereof.

In this embodiment the substance supply unit 119 is a multi-dose unit for delivering a plurality of metered doses of substance. In another embodiment the substance supply unit 119 could be a single-dose unit for delivering a single metered dose of substance.

In this embodiment the substance supply unit 119 is pre-primeable, here by loading a resilient element, and includes an actuation mechanism 141 which, when triggered, releases the resilient element and actuates the substance supply unit 119 to deliver a metered dose of substance through the nozzles 135*a, b* of the outlet unit 121.

In another embodiment the substance supply unit 119 could be manually actuated, for example, by manually depressing or compressing an applicator element.

Operation of the delivery device will now be described hereinbelow with reference to FIGS. 17 to 19 of the accompanying drawings.

Referring to FIG. 17, the nosepiece unit 117 is first inserted into one of the nasal cavities of a subject until the nosepiece member 123 abuts the nares of the nostril, such as sealingly to engage the skin-lined anterior section of the anterior region of the nasal cavity. When inserted, the distal end of the outlet unit 121 extends about 2 cm into the nasal cavity of the subject, which corresponds in position to that of the nasal valve.

Referring to FIG. 18, the subject then actuates the actuation mechanism 141, in this embodiment manually, which acts to actuate the substance supply unit 119 to deliver a metered dose of substance from the nozzles 135*a*, 135*b* of the outlet unit 121.

The metered dose of substance, in this embodiment in the form of an aerosol spray, is confined to the anterior region 127 of the nasal cavity. As described hereinabove, the present inventors have recognized that the systemic uptake of substance as delivered via the nasal cavity is, contrary to current thinking, enhanced where delivered through the anterior region 127 of the nasal cavity, and thus, by confining the delivered dose of substance to the anterior region 127, an enhanced systemic effect is obtained per unit dose of substance as compared to the conventional delivery of substances into the nasal cavity, such as generally by a nasal spray or nasal drops.

Following actuation, as illustrated in FIG. 19, the nosepiece unit 117 is withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 119. In a preferred embodiment, where the nosepiece unit 117 is replaceable, the nosepiece unit 117 can be replaced with a new nosepiece unit 117.

FIGS. 20 to 24 illustrate a nasal delivery device in accordance with a fifth embodiment of the present invention.

The delivery device comprises a housing 215, a nosepiece unit 217 for fitting in a nasal cavity of a subject through which substance is delivered to the nasal cavity, a substance supply unit 219 which is actuatable to deliver a metered dose of substance to the nosepiece unit 117, and a mouthpiece unit 2220 through which the subject exhales.

The nosepiece unit 217 comprises an outlet unit 221 which extends into the nasal cavity into which the nosepiece unit 117 is inserted, a first nosepiece member 223, in this embodiment a frusto-conical element, which is disposed to one, proximal end of the outlet unit 221 and is configured to obstruct, in this embodiment close, the nostril into which the nosepiece unit 217 is inserted, a second, expandable nosepiece member 225 which is disposed to the other, distal end of the outlet unit 221 and is configured, when expanded, to obstruct, in this embodiment close, the nasal cavity at a position therealong, in this embodiment at a position corresponding substantially to the nasal valve, such as to partition the nasal cavity into a first, anterior region 227 between the first and second nosepiece members 223, 225, which corresponds in volume to about one-third of the nasal cavity, and a second, posterior region 229, which corresponds in volume to about the remaining two-thirds of the nasal cavity, as illustrated in FIG. 22.

The outlet unit 221 comprises a support member 231, in this embodiment a narrow, elongate element, to which the first and second nosepiece members 223, 225 are supported, and at least one nozzle 235, in this embodiment a plurality of laterally-directed nozzles 235*a, b*, disposed between the first and second nosepiece members 223, 225 for delivering substance to the anterior region 227 of the nasal cavity.

In this embodiment the nozzles 235*a, b* are configured to provide an aerosol spray. In an alternative embodiment the nozzles 235*a, b* could be configured to deliver jets as columns of substance.

In this embodiment the second nosepiece member 225 comprises an inflatable member which is fluidly connected to the mouthpiece unit 220, such that, on exhalation by the subject through the mouthpiece unit 220, the second nosepiece member 225 is expanded to obstruct the nasal cavity in partitioning the same.

In this embodiment the substance supply unit 219 comprises a mechanical delivery pump, in particular a liquid delivery pump or a powder delivery pump, which delivers metered doses of substance on actuation thereof.

In another alternative embodiment the substance supply unit 219 could comprise a dry powder delivery unit which delivers metered doses of substance, as a dry powder, on actuation thereof.

In yet another alternative embodiment the substance supply unit 219 could comprise an aerosol canister which delivers metered volumes of a propellant, preferably a hydrofluoroalkane (HFA) propellant or the like, containing substance, either as a suspension or solution.

In yet another alternative embodiment the substance supply unit 219 could comprise a nebulizer which delivers metered doses of substance, as an aerosol spray, on actuation thereof.

In this embodiment the substance supply unit 219 is a multi-dose unit for delivering a plurality of metered doses of substance. In another embodiment the substance supply unit 219 could be a single-dose unit for delivering a single metered dose of substance.

In this embodiment the substance supply unit 219 is pre-primeable, here by loading a resilient element, and includes an actuation mechanism 241 which, when triggered, releases the resilient element and actuates the substance supply unit 219 to deliver a metered dose of substance through the nozzles 235*a, b* of the outlet unit 221.

In this embodiment the actuation mechanism 241 is a manually-actuated unit, but in another embodiment could be a breath-actuated unit which is actuated in response to the generation of a predetermined pressure at the mouthpiece unit 220, which is sufficient to provide for inflation of the second nosepiece member 225.

Operation of the delivery device will now be described hereinbelow with reference to FIGS. 21 to 24 of the accompanying drawings.

Referring to FIG. 21, the nosepiece unit 217 is first inserted into one of the nasal cavities of a subject until the first nosepiece member 223 abuts the nares of the nostril, such as sealingly to engage the skin-lined anterior section of the anterior region of the nasal cavity. When inserted, the distal end of the outlet unit 221 extends about 2 cm into the nasal cavity of the subject, which corresponds in position to that of the nasal valve.

Referring to FIG. 22, the subject then exhales through the mouthpiece unit 220, and the exhaled air flow acts to generate a pressure within the second nosepiece member 225, which is inflated such as to obstruct the nasal cavity and thereby partition the anterior and posterior regions 227, 229 of the nasal cavity.

Referring to FIG. 23, the subject then actuates the actuation mechanism 241, in this embodiment manually, which acts to actuate the substance supply unit 219 to deliver a metered dose of substance from the nozzles 235*a*, 235*b* of the outlet unit 221.

The metered dose of substance, in this embodiment in the form of an aerosol spray, is confined to the anterior region 227 of the nasal cavity as defined between the first and second nosepiece members 223, 225. As described hereinabove, the present inventors have recognized that the systemic uptake of substance as delivered via the nasal cavity is, contrary to current thinking, enhanced where delivered through the anterior region 227 of the nasal cavity, and thus, by confining the delivered dose of substance to the anterior region 227, an enhanced systemic effect is obtained per unit dose of substance as compared to the conventional delivery of substances into the nasal cavity, such as generally by a nasal spray or nasal drops.

Following actuation, as illustrated in FIG. 24, the nosepiece unit 217 is withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 219. In a preferred embodiment, where the nosepiece unit 217 is replaceable, the nosepiece unit 217 can be replaced with a new nosepiece unit 217.

In one alternative embodiment the second nosepiece member 225 could instead be mechanically expanded, for example, by expandable arm members.

FIGS. 25 to 28 illustrate a nasal delivery device in accordance with a sixth embodiment of the present invention.

The delivery device comprises a housing 315, a nosepiece unit 317 for fitting in a nasal cavity of a subject through which substance is delivered to the nasal cavity, a substance supply unit 319 which is actuatable to deliver metered doses of first and second substances to the nosepiece unit 317, and a mouthpiece unit 320 through which the subject exhales.

The nosepiece unit 317 comprises an outlet unit 321 which extends into the nasal cavity into which the nosepiece unit 317 is inserted, a first nosepiece member 323, in this embodiment a frusto-conical element, which is disposed to one, proximal end of the outlet unit 321 and is configured to obstruct, in this embodiment close, the nostril into which the nosepiece unit 317 is inserted, a second nosepiece member 325 which is disposed to the other, distal end of the outlet unit 321 and is configured to obstruct, in this embodiment close, the nasal cavity at a position therealong, in this embodiment at a position corresponding substantially to the nasal valve, such as to partition the nasal cavity into a first, anterior region 327 between the first and second nosepiece members 323, 325, which corresponds in volume to about one-third of the nasal cavity, and a second, posterior region 329, which corresponds in volume to about the remaining two-thirds of the nasal cavity, as illustrated in FIG. 26.

The outlet unit 321 comprises a support member 331, in this embodiment a narrow, elongate element, to which the first and second nosepiece members 323, 325 are supported, at least one first, anterior nozzle 335, in this embodiment a plurality of laterally-directed anterior nozzles 335*a, b*, which is disposed between the first and second nosepiece members 323, 325 for delivering substance, in this embodiment substance for systemic application, to the anterior region 327 of the nasal cavity, and at least one second, posterior nozzle 336, in this embodiment a single, axially-directed nozzle, for delivering substance, in this embodiment substance for topical or CNS application, to the posterior region 329 of the nasal cavity.

In this embodiment the anterior nozzles 335*a, b* are configured to provide an aerosol spray. In an alternative embodiment the anterior nozzles 335*a, b* could be configured to deliver jets as columns of substance.

In this embodiment the posterior nozzle 336 is configured to provide an aerosol spray. In an alternative embodiment the posterior nozzle 336 could be configured to deliver a jet as a column of substance.

In this embodiment the second nosepiece member 325 comprises a resilient element 337, here in the form of an annular skirt, which through its resilience acts to expand to obstruct the nasal cavity in partitioning the same. In an alternative embodiment the resilient element 337 could take the form of laterally-directed wings, which together act to obstruct the nasal cavity in partitioning the same.

In this embodiment the substance supply unit 319 comprises a mechanical delivery pump, in particular a liquid delivery pump or a powder delivery pump, which delivers metered doses of first and second substances on actuation thereof.

In another alternative embodiment the substance supply unit 319 could comprise a dry powder delivery unit which delivers metered doses of first and second substances, as dry powders, on actuation thereof.

In yet another alternative embodiment the substance supply unit 319 could comprise an aerosol canister which delivers first and second metered volumes of a propellant, preferably a hydrofluoroalkane (HFA) propellant or the like, each containing substance, either as a suspension or solution.

In yet another alternative embodiment the substance supply unit 319 could comprise a nebulizer which delivers metered doses of first and second substances, as aerosol sprays, on actuation thereof.

In this embodiment the substance supply unit 319 is a multi-dose unit for delivering a plurality of metered doses of first and second substances. In another embodiment the substance supply unit 319 could be a single-dose unit for delivering a single metered dose of first and second substances.

In this embodiment the substance supply unit 319 is pre-primeable, here by loading a resilient element, and includes an actuation mechanism 341 which, when triggered, releases the resilient element and actuates the substance supply unit 319 to deliver metered doses of first and second substances through the respective ones of the anterior nozzles 335a, b and posterior nozzle 336 of the outlet unit 321.

Operation of the delivery device will now be described hereinbelow with reference to FIGS. 26 to 28 of the accompanying drawings.

Referring to FIG. 26, the nosepiece unit 317 is first inserted into one of the nasal cavities of a subject until the first nosepiece member 323 abuts the nares of the nostril, such as sealingly to engage the skin-lined anterior section of the anterior region of the nasal cavity. When inserted, the distal end of the outlet unit 321 extends about 2 cm into the nasal cavity of the subject, which corresponds in position to that of the nasal valve, and the second nosepiece member 325 acts to obstruct the nasal cavity at that point such as to partition the nasal cavity.

Referring to FIG. 27, the subject then actuates the actuation mechanism 341, in this embodiment manually, which acts to actuate the substance supply unit 319 to deliver a metered dose of a first substance, in this embodiment substance for systemic application, from the anterior nozzles 335a, 335b of the outlet unit 321 and a metered dose of a second substance, in this embodiment substance for topical or CNS application, from the posterior nozzle 336 of the outlet unit 321.

The metered dose of the first substance, in this embodiment in the form of an aerosol spray, is confined to the anterior region 327 of the nasal cavity as defined between the first and second nosepiece members 323, 325. As described hereinabove, the present inventors have recognized that the systemic uptake of substance as delivered via the nasal cavity is, contrary to current thinking, enhanced where delivered through the anterior region 327 of the nasal cavity, and thus, by confining the delivered dose of substance to the anterior region 327, an enhanced systemic effect is obtained per unit dose of substance as compared to the conventional delivery of substances into the nasal cavity, such as generally by a nasal spray or nasal drops.

Following actuation, as illustrated in FIG. 28, the nosepiece unit 317 is withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 319. In a preferred embodiment, where the nosepiece unit 317 is replaceable, the nosepiece unit 317 can be replaced with a new nosepiece unit 317.

FIGS. 29 to 32 illustrate a nasal delivery device in accordance with a seventh embodiment of the present invention.

The delivery device comprises a housing 415, a nosepiece unit 417 for fitting in a nasal cavity of a subject through which substance is delivered to the nasal cavity, a substance supply unit 419 which is actuatable to deliver a metered dose of substance to the nosepiece unit 417, and a mouthpiece unit 420 through which the subject exhales.

The nosepiece unit 417 comprises a body unit 421 which comprises a first nosepiece member 423, in this embodiment a frusto-conical element, which is disposed at one, proximal end and is configured to obstruct, in this embodiment close, the nostril into which the nosepiece unit 417 is inserted, and a second nosepiece member 425 which is disposed to the other, distal end and comprises a flexible, elongate element which is sufficiently compliant to extend into, and in one embodiment, through the nasal valve. The second nosepiece member 425 has a shape, size and surface properties which enable the second nosepiece member 425 comfortably to penetrate the nasal valve. In this embodiment, when the nosepiece unit 417 is fully inserted into a nasal cavity, the distal end of the second nosepiece member 425 extends from about 3 cm to about 5 cm into the nasal cavity.

The nosepiece unit 417 further comprises at least one, in this embodiment a plurality of laterally-directed anterior nozzles 435a, b which are configured such as to deliver substance, in this embodiment substance for systemic application, to surfaces within the anterior region of the nasal cavity, and at least one second, posterior nozzle 436, in this embodiment a single, axially-directed nozzle, for delivering the substance to surfaces in an anterior section of the posterior region of the nasal cavity, in this embodiment an anterior third of the posterior region, and a preferred embodiment a mid-anterior third of the posterior region, as illustrated in FIG. 1(b).

In this embodiment the anterior nozzles 435a, b are configured to provide an aerosol spray. In an alternative embodiment the anterior nozzles 435a, b could be configured to deliver jets as columns of substance.

In this embodiment the posterior nozzle 436 is configured to provide an aerosol spray. In an alternative embodiment the posterior nozzle 436 could be configured to deliver a jet as a column of substance.

In this embodiment the substance supply unit 419 comprises a mechanical delivery pump, in particular a liquid delivery pump or a powder delivery pump, which delivers a metered dose of substance on actuation thereof.

In another alternative embodiment the substance supply unit 419 could comprise a dry powder delivery unit which delivers a metered dose of substance, as a dry powder, on actuation thereof.

In yet another alternative embodiment the substance supply unit 419 could comprise an aerosol canister which delivers a metered volume of a propellant, preferably a hydrofluoroalkane (HFA) propellant or the like, containing substance, either as a suspension or solution.

In yet another alternative embodiment the substance supply unit 419 could comprise a nebulizer which delivers a metered dose of substance, as an aerosol spray, on actuation thereof.

In this embodiment the substance supply unit 419 is a multi-dose unit for delivering a plurality of metered doses of substance. In another embodiment the substance supply unit 419 could be a single-dose unit for delivering a single metered dose of substance.

In this embodiment the substance supply unit 419 is pre-primeable, here by loading a resilient element, and includes an actuation mechanism 441 which, when triggered, releases the resilient element and actuates the substance supply unit 419 to deliver a metered dose of substance through the anterior nozzles 435a, b and the posterior nozzle 436. In this embodiment the actuation mechanism 441 is breath actuated in response to exhalation by the subject through the mouthpiece unit 420.

Operation of the delivery device will now be described hereinbelow with reference to FIGS. 30 to 32 of the accompanying drawings.

Referring to FIG. 30, the nosepiece unit 417 is first inserted into one of the nasal cavities of a subject until the first nosepiece member 423 abuts the nares of the nostril, such as sealingly to engage the skin-lined anterior section of the anterior region of the nasal cavity, and the second nosepiece member 425 extends into the nasal valve.

Referring to FIG. 31, the subject then exhales through the mouthpiece unit 420, which exhalation triggers the actuation mechanism 441, which in turn acts to actuate the substance supply unit 419 to deliver a metered dose of substance, in this embodiment substance for systemic application, from the anterior nozzles 435a, 435b and the posterior nozzle 436.

The substance as delivered from the anterior nozzles 435a, b is delivered to surfaces in the anterior region of the nasal cavity, and the substance as delivered from the posterior nozzle 436 is delivered to an anterior section of the posterior region of the nasal cavity, in this embodiment the anterior third of the posterior region of the nasal cavity, and more preferably substantially entirely to the mid-anterior third of the posterior region of the nasal cavity. As described hereinabove, the present inventors have recognized that the systemic uptake of substance as delivered via the nasal cavity is, contrary to current thinking, enhanced where delivered through the anterior region of the nasal cavity and the anterior third of the posterior region of the nasal cavity, and thus, by confining the delivered dose of substance to the anterior region and the anterior third of the posterior region of the nasal cavity, an enhanced systemic effect is obtained per unit dose of substance as compared to the conventional delivery of substances into the nasal cavity, such as generally by a nasal spray or nasal drops.

Following actuation, as illustrated in FIG. 32, the nosepiece unit 417 is withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 419. In a preferred embodiment, where the nosepiece unit 417 is replaceable, the nosepiece unit 417 can be replaced with a new nosepiece unit 417.

FIGS. 33 to 36 illustrate a nasal delivery device in accordance with an eighth embodiment of the present invention.

The delivery device comprises a housing 515, a nosepiece unit 517 for fitting in a nasal cavity of a subject through which substance is delivered to the nasal cavity, and a substance supply unit 519 which is actuatable to deliver a metered dose of substance to the nosepiece unit 517.

The nosepiece unit 517 comprises a body unit 521 which comprises a first nosepiece member 523, in this embodiment a frusto-conical element, which is disposed at one, proximal end and is configured to obstruct, in this embodiment close, the nostril into which the nosepiece unit 517 is inserted, a second nosepiece member 525 which is disposed to the other, distal end and comprises a flexible, elongate element which is sufficiently compliant to extend into, and in one embodiment, through the nasal valve, and a flow channel 527 which is fluidly connected to an actuation mechanism 541 of the substance supply unit 519, as will be described in more detail hereinbelow.

The nosepiece unit 517 further comprises at least one, in this embodiment a plurality of laterally-directed anterior nozzles 535a, b which are configured such as to deliver substance, in this embodiment substance for systemic application, to surfaces within the anterior region of the nasal cavity, and at least one second, posterior nozzle 536, in this embodiment a single, axially-directed nozzle, for delivering the substance to surfaces in an anterior section of the posterior region of the nasal cavity, in this embodiment an anterior third of the posterior region, and a preferred embodiment a mid-anterior third of the posterior region, as illustrated in FIG. 1(b).

In this embodiment the anterior nozzles 535a, b are configured to provide an aerosol spray. In an alternative embodiment the anterior nozzles 535a, b could be configured to deliver jets as columns of substance.

In this embodiment the posterior nozzle 536 is configured to provide an aerosol spray. In an alternative embodiment the posterior nozzle 536 could be configured to deliver a jet as a column of substance.

In this embodiment the substance supply unit 519 comprises a mechanical delivery pump, in particular a liquid delivery pump or a powder delivery pump, which delivers a metered dose of substance on actuation thereof.

In another alternative embodiment the substance supply unit 519 could comprise a dry powder delivery unit which delivers a metered dose of substance, as a dry powder, on actuation thereof.

In yet another alternative embodiment the substance supply unit 519 could comprise an aerosol canister which delivers a metered volume of a propellant, preferably a hydrofluoroalkane (HFA) propellant or the like, containing substance, either as a suspension or solution.

In yet another alternative embodiment the substance supply unit 519 could comprise a nebulizer which delivers a metered dose of substance, as an aerosol spray, on actuation thereof.

In this embodiment the substance supply unit 519 is a multi-dose unit for delivering a plurality of metered doses of substance. In another embodiment the substance supply unit 519 could be a single-dose unit for delivering a single metered dose of substance.

In this embodiment the substance supply unit 519 is pre-primeable, here by loading a resilient element, and includes an actuation mechanism 541 which, when triggered, releases the resilient element and actuates the substance supply unit 519 to deliver a metered dose of substance through the anterior nozzles 535a, b and the posterior nozzle 536. In this embodiment the actuation mechanism 541 is breath actuated in response to nasal exhalation by the subject, which nasal exhalation acts to generate a positive pressure in the nasal cavity, which is fluidly connected to the actuation mechanism 541 by the flow channel 527 of the nosepiece unit 517. The generation of a positive pressure in the nasal cavity also advantageously provides for expansion of the nasal cavity, which facilitates deposition on the surfaces within the nasal cavity.

Operation of the delivery device will now be described hereinbelow with reference to FIGS. 34 to 36 of the accompanying drawings.

Referring to FIG. 34, the nosepiece unit 517 is first inserted into one of the nasal cavities of a subject until the first nosepiece member 523 abuts the nares of the nostril, such as sealingly to engage the skin-lined anterior section of the anterior region of the nasal cavity, and the second nosepiece member 525 extends into the nasal valve.

Referring to FIG. 35, the subject then exhales, or at least attempts to exhale through the nasal cavity, which nasal exhalation triggers the actuation mechanism 441, which in turn acts to actuate the substance supply unit 519 to deliver a metered dose of substance, in this embodiment substance for systemic application, from the anterior nozzles 535*a*, 535*b* and the posterior nozzle 536.

The substance as delivered from the anterior nozzles 535*a, b* is delivered to surfaces in the anterior region of the nasal cavity, and the substance as delivered from the posterior nozzle 536 is delivered to an anterior section of the posterior region of the nasal cavity, in this embodiment the anterior third of the posterior region of the nasal cavity, and more preferably substantially to the mid-anterior third of the posterior region of the nasal cavity. As described hereinabove, the present inventors have recognized that the systemic uptake of substance as delivered via the nasal cavity is, contrary to current thinking, enhanced where delivered through the anterior region of the nasal cavity and the anterior third of the posterior region of the nasal cavity, and thus, by confining the delivered dose of substance to the anterior region and the anterior third of the posterior region of the nasal cavity, an enhanced systemic effect is obtained per unit dose of substance as compared to the conventional delivery of substances into the nasal cavity, such as generally by a nasal spray or nasal drops.

Following actuation, as illustrated in FIG. 36, the nosepiece unit 517 is withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 519. In a preferred embodiment, where the nosepiece unit 417 is replaceable, the nosepiece unit 517 can be replaced with a new nosepiece unit 517.

Finally, it will be understood that the present invention has been described in its preferred embodiments and can be modified in many different ways without departing from the scope of the invention as defined by the appended claims.

For example, in one embodiment the substance could be formulated such as to hinder mucociliary clearance, as would occur from the ciliated mucosal surfaces in the posterior region of the nasal cavity, and also prevent gravitational flow of the substance and dripping out of the substance from the nasal cavity. Typically, the formulation could have adhesive properties, for example, as a thixotropic formulation, and in one embodiment could be formulated in the manner of a gel.

In another embodiment the substance supply units 19, 119, 219, 319, 419, 519 of the above-described embodiments could be configured to deliver a combination of liquid and powdered substances.

REFERENCES

1. Cole, P, The Respiratory Role of the Upper Airway, Mosby, 1992, pages 7 and 8.
2. Daley-Yates, P T et al, Systemic bioavailability of fluticasone propionate administered as nasal drops and aqueous nasal spray formulations, Br J Clin Pharmacol, Jan 2001, 51(1), pages 103 to 105.
3. Harris A S et at, Intranasal administration of peptides: nasal deposition, biological response and absorption of desmopressin, J Pharm Sci, Nov 1986, 75(11), pages 1085 to 1088.
4. Rosenberger, H, Growth and Development of the Naso-Respiratory Area in Childhood, PhD Thesis, Laboratory of Anatomy, School of Medicine, Western Reserve University, Presented to the Annual Meeting of the American Laryngological, Rhinological and Otological Society, Charleston, South Carolina, USA, 1934.
5. Zacharek, M A et al, Sagittal and Coronal Dimensions of the Ethmoid Roof: A Radioanatomic Study, Am J Rhinol 2005, Vol 19, pages 348 to 352.

The invention claimed is:

1. A delivery device for delivering one or more substances to a nasal cavity of a subject for systemic uptake, the delivery device comprising:
   a nosepiece for insertion into the nasal cavity of the subject, the nosepiece including an outlet unit having a first nozzle; and
   a substance supply unit operable to deliver a first substance to the first nozzle;
   wherein the first nozzle is configured to deliver the first substance to: (i) either or both of a first region and/or a second region, or (ii) substantially only to the first region; and
   wherein the first region is an anterior region of the nasal cavity of the subject, the anterior region being anterior to a nasal valve of the subject, and the second region is an anterior section of a posterior region of the nasal cavity of the subject, the anterior section of the posterior region being posterior of the nasal valve of the subject; and
   a second nozzle configured to deliver a second substance to a third region, wherein the third region is a posterior section of the posterior region of the nasal cavity of the subject, the posterior section of the posterior region being posterior to the anterior section of the posterior region.

2. The delivery device of claim 1, wherein the first nozzle is further configured to deliver the first substance to a middle-third portion of the anterior section of the posterior region.

3. The delivery device of claim 1, wherein the substance supply unit is breath actuated by either oral exhalation of the subject or by nasal exhalation of the subject.

4. The delivery device of claim 1, wherein the substance supply unit is manually actuated.

5. The delivery device of claim 1, wherein the first nozzle is configured to deliver an aerosol spray, wherein the aerosol spray is a liquid aerosol or a powder aerosol.

6. The delivery device of claim 1, wherein the first nozzle is configured to deliver a liquid jet or a powder jet.

7. The delivery device of claim 1, wherein the first nozzle is configured to deliver the first substance substantially laterally with respect to a base portion of the nosepiece.

8. The delivery device of claim 1, further comprising a mouthpiece through which the subject in use exhales to cause closure of an oropharyngeal velum of the subject.

9. The delivery device of claim 1, wherein the outlet unit further comprises a posterior nosepiece member configured to obstruct the nasal cavity at a position therealong such that substantially all of the first substance delivered from the first nozzle is delivered to a region of the nasal cavity of the subject that is anterior of the posterior nosepiece member.

10. The delivery device of claim 9, wherein the posterior nosepiece member is configured to close the nasal valve.

11. The delivery device of claim 9, wherein the posterior nosepiece member comprises one of (i) an expandable member, (ii) a resilient member that self-expands upon insertion into the nasal cavity of the subject to obstruct and partition the nasal cavity of the subject when expanded, or (iii) an inflatable member configured to be inflated subsequent to insertion into the nasal cavity of the subject to obstruct and partition the nasal cavity of the subject when inflated.

12. The delivery device of claim 9, further comprising a mouthpiece through which the subject in use exhales to cause closure of an oropharyngeal velum of the subject, wherein the mouthpiece is fluidly connected to the posterior nosepiece member, whereby in use exhaled air from an exhalation breath of the subject inflates the posterior nosepiece member.

13. The delivery device of claim 9, wherein the outlet unit further includes an anterior nosepiece member configured to obstruct an opening of the nasal cavity of the subject anterior to the nasal valve.

14. The delivery device of claim 1, wherein the outlet unit further includes an anterior nosepiece member configured to obstruct an opening of the nasal cavity of the subject anterior to the nasal valve.

15. The delivery device of claim 1, wherein the outlet unit further comprises a posterior nosepiece member configured to obstruct the nasal cavity at a position therealong, such that (i) substantially all of a dose of the first substance delivered from the first nozzle is delivered to a region of the nasal cavity of the subject anterior of the posterior nosepiece member, and (ii) substantially all of the dose of the second substance delivered from the second nozzle is delivered to a region of the nasal cavity of the subject posterior of the posterior nosepiece member.

16. The delivery device of claim 15, wherein the posterior nosepiece member comprises one of (i) an expandable member, (ii) a resilient member that self-expands upon insertion into the nasal cavity of the subject to obstruct and partition the nasal cavity of the subject when expanded, or (iii) an inflatable member configured to be inflated subsequent to insertion into the nasal cavity of the subject to obstruct and partition the nasal cavity of the subject when inflated.

17. The delivery device of claim 1, wherein the first substance and the second substance are different substances.

18. The delivery device of claim 1, wherein the first substance and the second substance are the same substance.

* * * * *